(12) United States Patent
Lundgren et al.

(10) Patent No.: US 9,566,604 B2
(45) Date of Patent: Feb. 14, 2017

(54) METHOD FOR PREPARING A SURFACE WITH A CONTROLLED COVERAGE OF NANOGRADE PARTICLES

(75) Inventors: Anders Lundgren, Varberg (SE); Mattias Berglin, Göteborg (SE); Hans Elwing, Askim (SE); Mats Hulander, Göteborg (SE)

(73) Assignee: CLINE SCIENTIFIC AB, Goeteborg (SE)

( * ) Notice: Subject to any disclaimer, the term of this patent is extended or adjusted under 35 U.S.C. 154(b) by 836 days.

(21) Appl. No.: 13/818,541

(22) PCT Filed: Aug. 24, 2011

(86) PCT No.: PCT/EP2011/064582
§ 371 (c)(1),
(2), (4) Date: Mar. 22, 2013

(87) PCT Pub. No.: WO2012/025576
PCT Pub. Date: Mar. 1, 2012

(65) Prior Publication Data
US 2013/0180326 A1    Jul. 18, 2013

(30) Foreign Application Priority Data
Aug. 24, 2010    (SE) ....................... 1050866

(51) Int. Cl.
*B05D 1/00*    (2006.01)
*B05D 1/18*    (2006.01)
(Continued)

(52) U.S. Cl.
CPC ................ *B05D 1/007* (2013.01); *B05D 1/18* (2013.01); *G01N 19/04* (2013.01); *B05D 1/20* (2013.01);
(Continued)

(58) Field of Classification Search
None
See application file for complete search history.

(56) References Cited

U.S. PATENT DOCUMENTS 5,609,907 A    3/1997  Natan
6,025,202 A    2/2000  Natan
(Continued)

FOREIGN PATENT DOCUMENTS

WO    WO-98/10289 A1    3/1998
WO    WO-03/027679 A1    4/2003
(Continued)

OTHER PUBLICATIONS

Huwiler et al.; Functionalizable Nanomorphology Gradients via Colloidal Self-Assembly; Langmuir; 2007, 23, 5929-5935.*
(Continued)

*Primary Examiner* — Michael P Rodriguez
(74) *Attorney, Agent, or Firm* — Saliwanchik Lloyd & Eisenschenk

(57) ABSTRACT

The present invention regards nano surfaces and particularly a gradient based nano surface. According to embodiments of the invention a surface bound gradient is created by distributed nanoparticles along a plane surface. This procedure greatly reduces the number of prepared surfaces needed, as well as the methodological error of analysis of adsorption and adhesion phenomena.

9 Claims, 18 Drawing Sheets

(51) Int. Cl.
*G01N 19/04* (2006.01)
*B05D 1/20* (2006.01)
*B05D 5/04* (2006.01)
*B05D 5/08* (2006.01)
*B82Y 30/00* (2011.01)

(52) U.S. Cl.
CPC . *B05D 5/04* (2013.01); *B05D 5/08* (2013.01); *B82Y 30/00* (2013.01); *Y10T 428/249921* (2015.04); *Y10T 428/25* (2015.01); *Y10T 428/26* (2015.01)

(56) References Cited

U.S. PATENT DOCUMENTS

| | | |
|---|---|---|
| 6,242,264 B1 | 6/2001 | Natan et al. |
| 7,332,327 B2 | 2/2008 | Vikholm et al. |
| 7,390,532 B2 | 6/2008 | Dellwo et al. |
| 7,510,882 B2 | 3/2009 | Vikholm et al. |
| 2003/0059954 A1 | 3/2003 | Vikholm et al. |
| 2003/0157732 A1 | 8/2003 | Baker et al. |
| 2003/0170480 A1 | 9/2003 | Gorman et al. |
| 2004/0265392 A1 | 12/2004 | Tovar et al. |
| 2005/0106570 A1 | 5/2005 | Kataoka et al. |
| 2006/0003097 A1 | 1/2006 | Andres et al. |
| 2006/0034065 A1 | 2/2006 | Thurk |
| 2007/0125181 A1 | 6/2007 | Ofek et al. |
| 2007/0127164 A1 | 6/2007 | Ofek et al. |
| 2007/0138583 A1 | 6/2007 | Ofek et al. |
| 2008/0038830 A1 | 2/2008 | Ure et al. |
| 2008/0045736 A1 | 2/2008 | Ying et al. |
| 2009/0098366 A1 | 4/2009 | Smoukov et al. |
| 2009/0221447 A1 | 9/2009 | Mur et al. |
| 2010/0086488 A1 | 4/2010 | Hoheisel et al. |
| 2011/0045180 A1 | 2/2011 | Hsing et al. |
| 2011/0245528 A1 | 10/2011 | Schwartz |

FOREIGN PATENT DOCUMENTS

| | | |
|---|---|---|
| WO | WO-03/058292 A1 | 7/2003 |
| WO | WO-03/083478 A1 | 10/2003 |
| WO | WO-2007/057905 A2 | 5/2007 |
| WO | WO-2007/057906 A2 | 5/2007 |
| WO | WO-2007/057912 A2 | 5/2007 |
| WO | WO-2010/036195 A1 | 4/2010 |

OTHER PUBLICATIONS

Lundgren et al.; Self-Arrangement Among Charge-Stabilized Gold Nanoparticles on a Dithiothreitol Reactivated Octanedithiol Monolayer; Nano Letters, 2008, vol. 8, No. 11, 3989-3992.*
International Search Report in International Application No. PCT/EP2011/064582, filed Aug. 24, 2011.
Adamczyk, Z., et al., "Structure and Ordering in Localized Adsorption of Particles," Journal of Colloid and Interface Science, vol. 140, No. 1, Nov. 1990, pp. 123-137.
Elwing, H., et al., "A Wettability Gradient Method for Studies of Macromolecular Interactions at the Liquid/Solid Interface," Journal of Colloid and Interface Science, vol. 119, No. 1, Sep. 1987, pp. 203-210.
Johnson, C., et al., "Adsorption of Charged latex Particles on Mica Studied by Atomic Force Microscopy," Journal of Colloid and Interface Science, vol. 179, Article 0253, 1996, pp. 587-599.
Kim, M., et al., "Gradient polymer surfaces for biomedical applications," Progress in Polymer Science, vol. 33, 2008, pp. 138-164.
Hanarp, P., et al., "Control of nanoparticle film structure for colloidal lithography," Colloids and Surfaces A: Physiochem. Eng. Aspects, vol. 214, 2003, pp. 23-36.
Arnold, M., et al., "Activation of Integrin Function by Nanopatterned Adhesive Interfaces," ChemPhysChem, vol. 5, 2004, pp. 383-388.
K'Owino, I., et al., "Impedance Spectroscopy: A Powerful Tool for Rapid Biomolecular Screening and Cell Culture Monitoring," Electroanalysis, vol. 17, No. 23, 2005, pp. 2101-2113.
Morgenthaler, S., et al., "Surface-chemical and-morphological gradients," The Royal Society of Chemistry, vol. 4, 2008, pp. 419-434.
Andersson, O., et al., "Gradient Hydrogel Matrix for Microarray and Biosensor Applications: An Imaging SPR Study," Biomacromolecules, vol. 10, No. 1, 2009, pp. 142-148.
Grabar, K., et al., "Kinetic Control of Interparticle Spacing in Au Colloid-Based Surfaces: Rational Nanometer-Scale Architecture," Journal of American Chemistry Society, vol. 118, 1996, pp. 1148-1153.
Zhao, J., et al., "Nanoparticle-Mediated Electron Transfer Across Ultrathin Self-Assembled Films," J. Phys. Chem. B, vol. 109, No. 48, 2005, pp. 22985-22994.
Liedberg, B., et al., "Molecular Gradients of ω-Substituted Alkanethiols on Gold: Preparation and Characterization," Langmuir, vol. 11, No. 10, 1995, pp. 3821-3827.
Kooij, E., et al., "Ionic Strength Mediated Self-Organization of Gold Nanocrystals: An AFM Study," Langmuir, vol. 18, No. 20, 2002, pp. 7677-7682.
Michel, R., et al., "A Novel Approach to Produce Biologically Relevant Chemical Patterns at the Nanometer Scale: Selective Molecular Assembly Patterning Combined with Colloidal Lithography," Langmuir, vol. 18, No. 22, 2002, pp. 8580-8586.
Semmler, M., et al., "Diffusional Deposition of Charged Latex particles on Water-Solid Interfaces at Low Ionic Strength," Langmuir, vol. 14, No. 18, 1998, pp. 5127-5132.
Arnold, M., et al., "Induction of Cell Polarization and Migration by a Gradient of Nanoscale Variations in Adhesive Ligand Spacing," Nano Letters, vol. 8, No. 7, 2008, pp. 2063-2069.
Lundgren, A., et al., "Self-Arrangement Among Charge-Stabilized Gold Nanoparticles on a Dithiothreitol Reactivated Octanedithiol Monolayer," Nano Letters, vol. 8, No. 11, 2008, pp. 3989-3992.
Bard, A., et al., "Electrochemical Methods: Fundamentals and Applications," John Wiley & Sons, Inc., $2^{nd}$ Ed., pp. 26-28.
Verwey, E., et al., "Theory of the Stability of Lyophobic Colloids: The Interaction of Sol Particles Having an Electric Double Layer," Elsevier Publishing Co., 1948, pp. 1-205.

* cited by examiner

FIG. 2
Prior Art
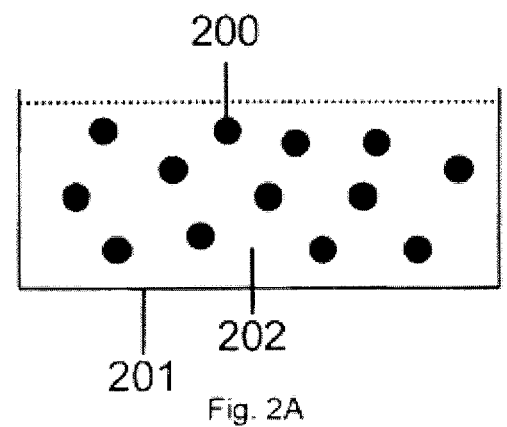
Fig. 2A
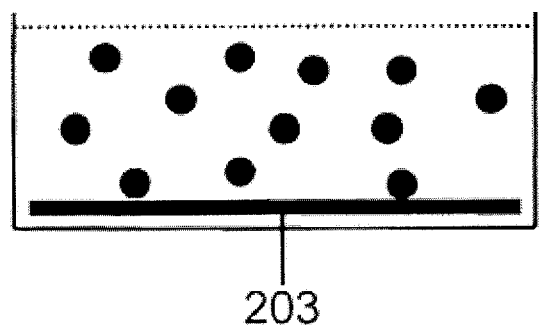
Fig. 2B
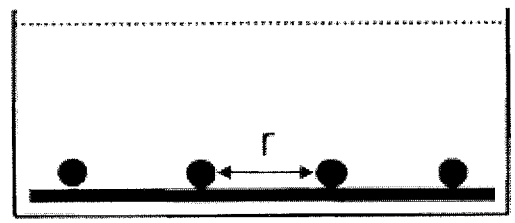
Fig. 2C

Side view

METHOD FOR PREPARING A SURFACE WITH A CONTROLLED COVERAGE OF NANOGRADE PARTICLES

CROSS-REFERENCE TO RELATED APPLICATIONS

This application is the U.S. national stage application of International Patent Application No. PCT/EP2011/064582, filed Aug. 24, 2011, which claims priority to Swedish Application No. 1050866-1, filed Aug. 24, 2010, the disclosures of each of which are incorporated herein by reference in their entirety.

FIELD OF THE INVENTION

This invention pertains in general to the field of surface chemistry. More particularly the invention relates to surfaces with nano scale properties.

BACKGROUND

The problem with solid surface interactions with living biological tissue is a repeating subject within areas of medical technology, e.g. biomaterials, biosensors, and controlled drug delivery. Other application areas are food processing technology and biotechnical process chemistry, areas where wanted or unwanted interactions with biologically produced substances exist. Thus, there is a constant need for new materials with improved functions and characteristics, and there is an increasing need of experimental surface modifications suitable for the specific application areas.

The field of nanotechnology has made great progresses during the last decades, mainly due to the fact that nanostructured materials, with a structure size of 1-1000 nm, have very interesting properties with regards to optimized interaction with biological fluids and living tissue. Central to this patent application is a recently published paper describing a method of making nanostructured solid surfaces with nanostructures around 10 nm [1]. The method includes that flat gold surfaces are allowed to react with thiol terminated, lineary alkanes (dithiols), binding to the gold surface with one thiol group, whereas the other thiol end will constitute an overlayering carpet of pristine thiol groups.

A stable colloidal solution of negatively charged gold particles in the size range of 8-12 nm was brought into contact with the surface and the gold particles were adsorbed to the aforementioned pristine thiol groups. It was observed that the distance between the adsorbed particles could be controlled by varying the ionic strength of the citrate buffer that was used during the adsorption. The distance (center to center) could be varied between 10-100 nm when the molarity (concentration) of the buffer was varied between 10-0 nM as judged from visualization experiments with scanning electron microscopy (SEM). Similar results have earlier been demonstrated in particle adsorption experiments with electrostatically stabilized solutions of surface charged polymer particles to mineral surfaces such as glass, silicon dioxide or mica [2-5]. In addition, similar results have also been presented concerning adsorption of negatively charged gold surface nanoparticles from electrostatic stabilized solutions to glass surfaces or silicon dioxid surfaces that are positively charged due to chemical modifications [6].

The principle of electrostatically controlled particle adsorption is shown in FIG. 2. An electrostatically stabilized solution 202 containing surface charged nanoparticles 200 is applied to a beaker 201 (FIG. 2A). A surface preparation 203 is introduced in the container (FIG. 2B) allowing the particles 200 to bind to the surface 203 by means of electrostatic, semi-covalent, covalent or other types of bindings, leading to that a stable adsorption is obtained after a certain time (FIG. 2C). The particles have a certain distance, r, from each other.

This condition represents a terminal condition for the adsorption, and prolonged incubation time does not have any further impact on surface coverage of particles. When the surface is removed from the particle solution, the distance between two adjacent particles can be estimated from the interaction pair-potential according to the DLVO-theory [1,7], FIG. 3.

In short, the pair potential $U(r)$, where r is the distance between two particles, may be calculated as the sum of an attractive potential $U_{attraction}(r)$ emanating from the dispersive forces between the particles as well as a repulsive potential $U_{repulsion}(r)$ emanating from the electrostatic repulsion between the particles.

The shape of the repulsive potential can be calculated in different ways, but will always vary with the so called Debye-distance which is an approximate measure of the declination of the potential outside the surface of the particle. A short Debye-distance means that the repulsive potential is rapidly declining outside the surface of the particle. The Debye distance is in turn dependent of the ionic strength in the particle solution 202, and can be expressed as:

$$\kappa^{-1} = \left[\frac{\varepsilon\varepsilon_0 kT}{1000 e^2 N_A 2I}\right]^{1/2}$$

where $\varepsilon$ is the relative permittivity, $\varepsilon_0$ is the permittivity I in vacuum, k is the Boltzmann constant, T is the temperature, e is the elementary charge, $N_A$ is Avogadro's constant and the ionic strength is:

$$I = \frac{1}{2}\sum_{i=1}^{n} c_i z_i^2$$

where $c_i$ and $z_i$ is the molar concentration and the charge of an i ion in the solution.

The Debye-distance, and the range of the repulsive potential, is therefore reduced with increasing ionic concentration in the colloidal solution 202. This means that each particle can bind closer to other particles on the surface when the condition $$\frac{U(r)}{kT} = \frac{1}{\lambda}$$

where $U(r)$ is the pair potential, kT is the thermal energy, and $\lambda$ is a constant, is fulfilled for smaller r.

Surfaces prepared with dithiols and gold nanoparticles as described above and in [1, 8] have been used in biological experiments. In these experiments, the spaces between the particles were made protein repelling with a conjugated maleimide reagent which rapidly binds covalently to dithiol groups. The maleimides were conjugated with polyethylene glycol (PEG) which resulted in the spaces between the particles becoming repelling for proteins and cells. The surface on the absorbed gold particles could later be modified with thiol reagents, e.g. thiol with methyl groups, which gives the adsorbed gold particles hydrophobic characteristics. Surfaces with gold particles made in this way has a very highly controlled chemical structure and physical organization in the nanometer range which makes such surfaces well suited for adhesion studies of different kinds. The described method is very flexible for adhesion studies due to the relatively large number of commercial substances with malemide functions which can bind between the adsorbed particles, as well as thiol reagents which can bind to the adsorbed gold particles.

Similar experiments have been performed where gold nanoparticles, stabilized by polymers, have been applied to silica and glass surfaces by so called "dip-coat" technology [9]. Note that this method does not utilize electrostatic repulsion between particles to control their spread throughout the surface but instead the distance is defined by the polymer structures that surround the particles in solution. Interaction between these particles and the adsorbed surface is weak, why the particles after adsorption must be sintered in the substrate, a process in which also the surrounding polymers disappears from the surface. The surface around the gold particles then becomes the underlying silica substrate which can be modified with functional silanes, e.g. PEG-modified silanes, which makes this surface resistant to bioadhesion. The particles' surfaces can be modified with thiol reagents, e.g. thiol conjugated to so called RGD-peptides, an amino acid sequence which mediates cell interactions.

In this experiment it has also been described that polymer particles in an electrostatic stabilized solution is adsorbed to charged mineral surfaces and that the distance between the adsorbed particles has been controlled with electrostatic repulsion according to the above description [10]. The adsorbed surfaces either have a native net charge, or have been charged through chemical modification, e.g. with functional silanes. The bond between the surface and particles has primarily been of electrostatic nature. The surfaces with the adsorbed polymer particles have been used as a lithographic template with which the polymer particle covered parts of the surface have been transformed to isles of gold in the size range of 10-1000 nm surrounded by the substrate surface material. The surrounding substrate surface was then modified, e.g. with poly-L-lysine-PEG. Lysine is a positively charged polymer, which is adsorbed by negatively charged surfaces, and when conjugated with PEG, in certain cases make these surfaces resistant to bio adhesion. The gold surfaces can then be modified with thiol reagents, e.g. linear alkane thiols, which make the gold surfaces hydrophobic. To these hydrophobic surfaces proteins can be adsorbed, e.g. the protein laminin. Such surfaces have been used to study cell proliferation and surface interaction.

All of the above described technologies can be used to study the importance of a surface nanostructure for the adhesion process, and can be used as a platform for the design of materials with desired biological characteristics.

Most adhesion studies are performed on surfaces with a constant chemical setup. When studying the importance of one type of surface modification it is common practice to use several surface preparations in order to analyze adhesion phenomena independently. This procedure, however, is time and labor consuming since several surface preparations must be prepared for each series of experiments. In addition, the methodological errors of measurements can be relatively large which means that the interpretation of the intended study of adhesion phenomena can be either incorrect or overlooked.

A method to limit the methodological error and to reduce time spent to prepare surfaces is to create gradients in the chemical characteristics on a surface. One example of such a method is the so called "wettability gradient", a surface which is hydrophobic in one end and hydrophilic in the other [11]. Between these endpoints the controlled and continuous gradient of chemical characteristics is found. This type of surface gradient significantly reduces time to prepare as well as the methodological error, and is often used in academic research [12-14].

Several methods to prepare continuous chemical gradients on a surface are known, one of them the well known diffusion method, FIG. 1. In this case the method of action is such that a reagent 001, e.g. methylchlorosilane is mixed in a solvent with high density 002, e.g. trichloroethyleneacetate (tri-). The mixture is then layered under a different solvent 003, e.g. xylene with low density. Between these layers there is a surface 004, e.g. glass on which a gradient will form. In time the solvents start to diffuse into each other where also the set of reagent 001 diffuses and binds to the surface 004. At a specific time of diffusion a bound gradient of hydrophobic methyl groups has occurred on the hydrophilic glass surface [11]. How much of the reagent that binds to the surface at a certain position, and therefore the hydrophobicity at this position is determined by the concentration of the set of reagents 001 on the surface at this position in combination with the time during which the surface has been exposed to the reagent solution. This means that the characteristics of the obtained gradient are determined through kinetic control.

To manufacture an even gradient in particle density with the above described method should be difficult, since the binding of nanoparticles from an electrostatic stabilized solution to a surface which binds these particles usually is a very fast process in relation to the particles rate of diffusion. This is low compared to the rate of diffusion for small molecules, such as methylchlorosilane. Attempts made to control the distance between nanoparticles on surfaces, where nanoparticles has been adsorbed to binding surfaces from electrostatic stabilized solutions, through varying the particle concentration and time of incubation, has shown the difficulties in controlling low density gradients of particles. Also, the particles do not show the same conformity of organization on the surface as they do after electrostatic controlled adsorption as described above [6, 15].

Recently, a gradient of gold particles on a silica substrate was disclosed, where the structuring of bound particles was good [16]. This gradient, described in [16] was manufactured according to a modified "dip-coat"-method, but without using electrostatic control or diffusion gradients. The obtained gradient had limited dynamic and the smallest particle distance was about 50 nm. The gradients were modified chemically with PEG between the particles and RGD peptides on top of the particles. The gradient surfaces were subsequently used in experiments to investigate cellular adhesion. In general, this publication discloses that the interest to make surface bound density gradients of gold particles is great, for reasons mentioned above. The technical solution to produce gradients according to [16] is however significantly more complex than the present invention.

SUMMARY

Accordingly, the present invention preferably seeks to mitigate, alleviate or eliminate one or more of the above-identified deficiencies in the art and disadvantages singly or in any combination and solves at least the above mentioned problems by providing a method, a surface, a product and a use according to the appended claims.

According to a first aspect a method for preparing a continuous gradient of deposited and electrically charged nanoparticles along a solid surface is provided, wherein the number of deposited and electrically charged nanoparticles per unit area of the surface is relatively high on one end of the surface and relatively low on the opposite end of the surface. The distance between the deposited particles, at the time of deposition, is regulated through electrostatic repulsion between the nanoparticles in a solution. The degree of electrostatic repulsion of particles in the solution is obtained by a diffusion of a salt solution into the solution comprising nanoparticles.

This is advantageous, because it allows forming an improved gradient of nanoparticles on a surface.

The diffusion of salt solution may be obtained by forming a layer of a salt solution with relatively high density and concentration under a layer of substantially salt free solution comprising nanoparticles, and that the continuous gradient may be regulated by the time of diffusion and concentration of salt in the salt solution.

In an embodiment, the diffusion of the salt solution may be obtained by keeping the salt solution in a reservoir, placed into contact with the suspension of nanoparticles further comprising a matrix allowing diffusion of nanoparticles but prohibiting convection currents, and which suspension of nanoparticles is in contact with the solid surface.

This is advantageous, since it allows forming gradients in two dimensions.

The nanoparticles may consist of metal, ceramics, such as glass, or polymer material.

The solid surface may consist of metal, ceramics, such as glass, or polymer material.

The bonding forces between the nanoparticles and the surface may comprises covalent bonds, Coulombic interactions, metal bonds, van der Waals bonds, hydrogen bonds, dipole-dipole bonds or ion-dipole bonds.

In an embodiment, the surface is gold, with bound dithiol reagent and the nanoparticles are covalently bound to thiol groups of the dithiol molecules bound to the gold surface.

In an embodiment, negatively charged but non-surface binding particles are mixed with surface binding nanoparticles.

This is advantageous, since it may improve dispersion and prevent cluster formation of the surface binding nanoparticles.

The method may further comprising adding a first separate surface and a second separate surface to the surface, wherein the first separate surface has a surface chemistry similar to the nanoparticle and the second separate surface has a surface chemistry similar to the surface.

In an embodiment, scale marks are added to the surface.

An advantage with this is that it may simplify microscopic analysis of adhesion analysis.

According to a second aspect, a surface is provided, with a continuous gradient of deposited and electrically charged nanoparticles.

The gradient length may be between 1 mm and 50 mm.

The nanoparticles may have an average diameter between 10 and 60 nm.

The average distance of the nanoparticles may be about 10-60 nm in one end of the gradient and about 100-150 nm in the other end of the gradient.

In an embodiment, the gradient is linear.

The nanoparticles and/or the surface may consist of metal, ceramics, such as glass, or polymer material.

The nanoparticles and/or the surface may have a compound conjugated to them. The compound may be selected from the group consisting of thiol groups, such as methyl terminated, amino terminated, acid terminated, peptide terminated, saccharide-conjugated or PEG-conjugated thiol, or thiol silane; PEG, such as poly-L-lysine-PEG, PEG-modified silanes, malemide-PEG; and aminosilane.

According to a third aspect, a device for analysis of adhesion phenomena is provided, comprising a gradient surface according to the second aspect, a first separate surface and a second separate surface, wherein the surfaces are separated and the first separate surface has a surface chemistry similar to the nanoparticle and the second separate surface has a surface chemistry similar to the surface.

The nanoparticles, the surface, the first separate surface or the second separate surface may have the same or different compound/s conjugated to them, and the compound/s may be selected from the group consisting of thiol groups, such as methyl terminated, amino terminated, acid terminated, peptide terminated, saccharide-conjugated or PEG-conjugated thiol, or thiol silane; PEG, such as poly-L-lysine-PEG, PEG-modified silanes, malemide-PEG; and aminosilane.

According to a fourth aspect, use the surface according to the second aspect, or the device according to third aspect, for adhesion analysis is provided.

The analysis may be based on surface plasmon resonance (SPR), electrochemistry, light microscopy or scanning electron microscopy (SEM).

The present invention provides the advantage over the prior art that it allows forming an improved gradient of nanoparticles on a surface.

BRIEF DESCRIPTION OF THE DRAWINGS

These and other aspects, features and advantages of which the invention is capable, will be apparent and elucidated from the following description of embodiments of the present invention, reference being made to the accompanying drawings, in which FIGS. 1 and 2 are illustrations of prior art methods;

DESCRIPTION OF EMOBIDMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

According to one aspect of the invention, a method for the convenient manufacture of surfaces with adsorbed nanoparticles with a gradient is provided. In an embodiment, the method may be described as follows.

1. One-dimensional Diffusion

Figure 4:
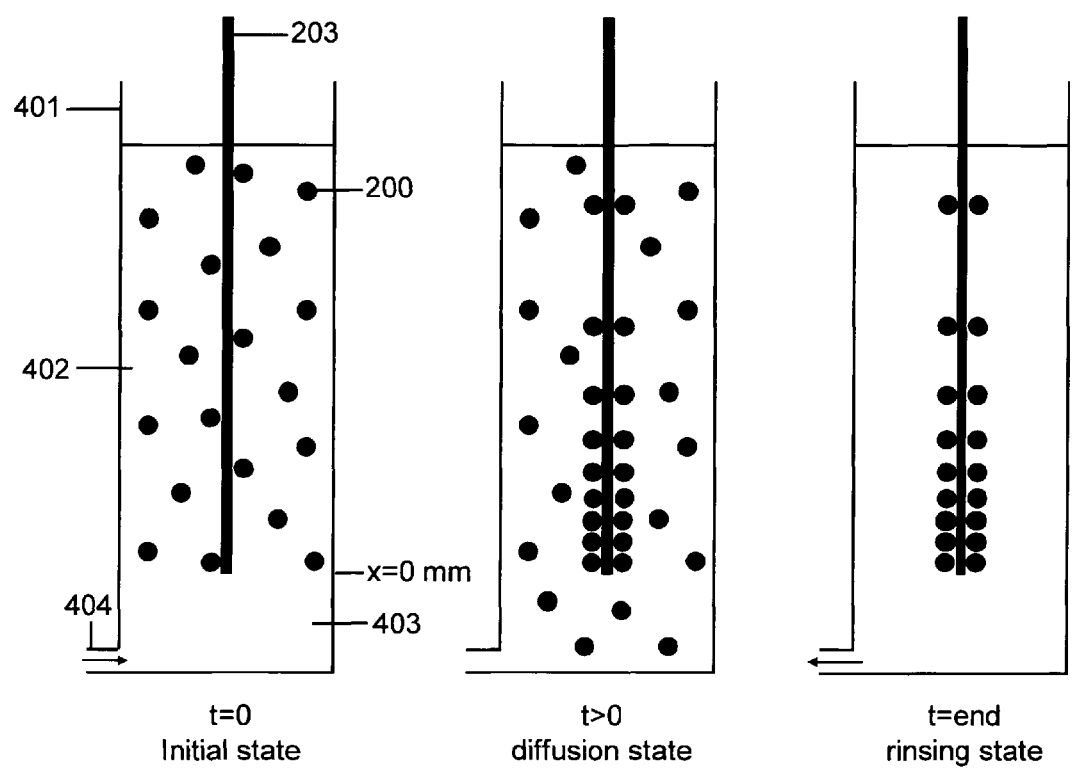
FIG. 4 is an illustration of the method according to an embodiment.

In an embodiment according to FIG. 4, a plane surface 203 with the ability to bind electrostatic surface charged nanoparticles 200 from an electrostatically stabilized particle solution is put in a vial 401. A salt free, or almost salt free, solution 402 with surface charged particles 200 is then added to the vial. A salt solution 403 with a relatively high density is carefully layered under the salt free solution 402 in a way so that the gravity dependent phase level between the solutions 403 and 402 is leveled with the lower part of the surface 203. In time, the salt solution 403 will diffuse into the salt free solution 402 and form a gradient of ionic strength in this.

As will be appreciated by a person skilled in the art, the surface does not need to be plane, but may have any kind of curvature or shape.

The electrostatic dependent repulsion between the particles is reduced when the ionic strength in the buffer close to the surface 203 increases. The particles therefore adsorb gradually closer to each other on the surface with the highest density of particles closest to the original phase level between the solutions 402 and 403. The lowest density of particles is found in the upper layer of the vial where the ionic strength is low and therefore the electrostatic repulsion is highest. After a controlled time of diffusion the solution is emptied from the vial, from below through the same tube 404 which was used when layering the salt solution 403 under particle containing salt free solution 402.

In absence of convection and that the distance from the surface lower level, x=0 mm, to the bottom of the vial is sufficient, and that the distance from the surface lower level, x=0 mm, to the surface of the salt free solution 402 is sufficient, and that the diffusion is not allowed to continue for too long, the gradual distribution of the salt concentration in the solution above the surface 203 can be described with Fick's 2nd law of diffusion in one dimension:

$$\frac{\partial c}{\partial t} = D\frac{\partial^2}{\partial x^2}c$$

wherein, for the above mentioned conditions:

$$c(x, t) = \frac{1}{2}c_0\left(1 - \operatorname{erf}\frac{x}{2\sqrt{Dt}}\right)$$

where c is the molar salt concentration, x is the position in the vial in the relation x=0 (which coincides with the lower level of the surface 203), t is the time of diffusion, $c_0$ is the salt concentration in the solution 403 at t=0, and D is the diffusion constant for the salt in question.

This means that the length and the slope of the acquired particle gradient can be varied through changing the initial salt concentration $c_0$ and the time of diffusion t which gives the method of manufacturing great flexibility.

Figure 5:
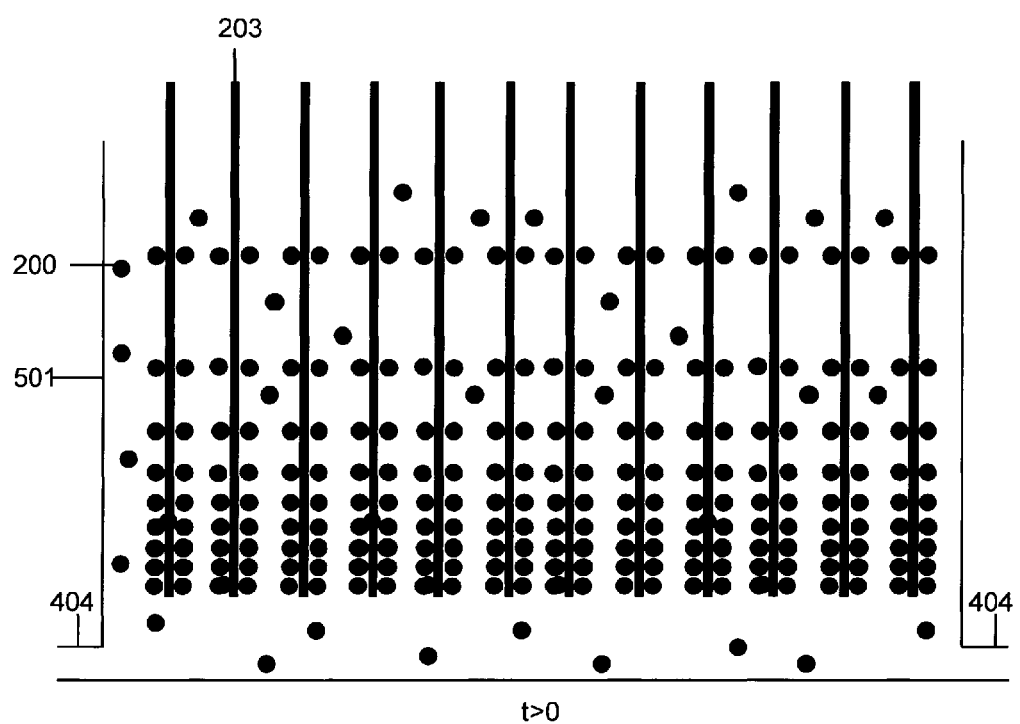
FIG. 5 is an illustration of the method according to another embodiment.

Further development of the invention described in FIG. 5 uses vials 501 which allow several surfaces to be used at the same procedure of diffusion as described in FIG. 4. An advantage of this method is that all surfaces in the vial will be exposed to the same solution of gold particles, molarity of the salt solution, and the time of diffusion. This assures that surfaces can be prepared with a high rate of conformity at the same preparation.

Figure 1:
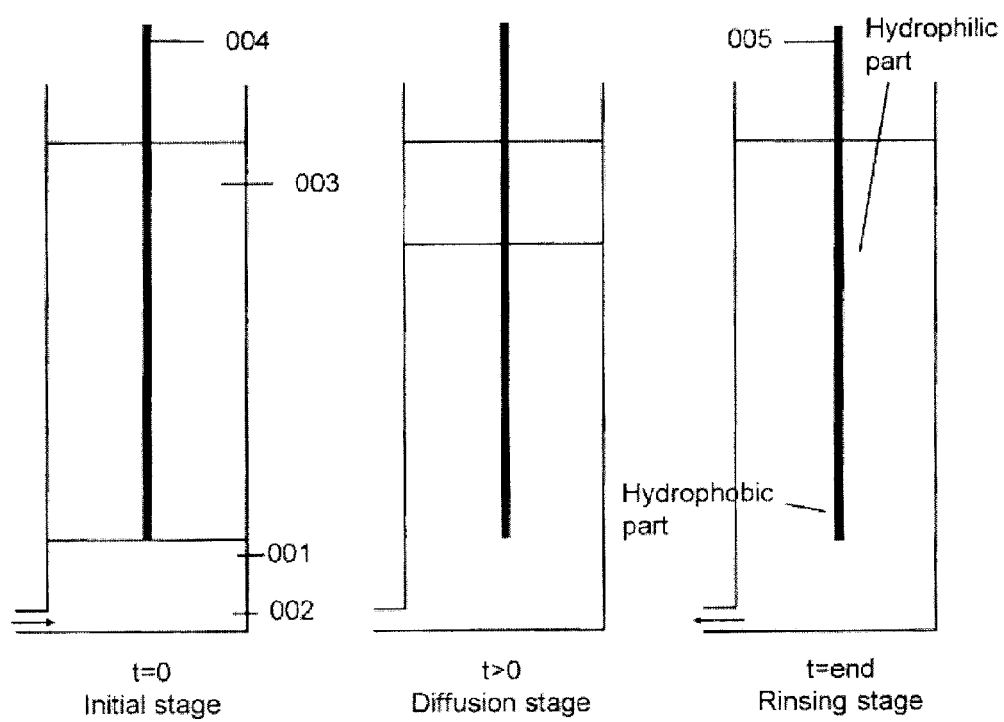
Figure 3:
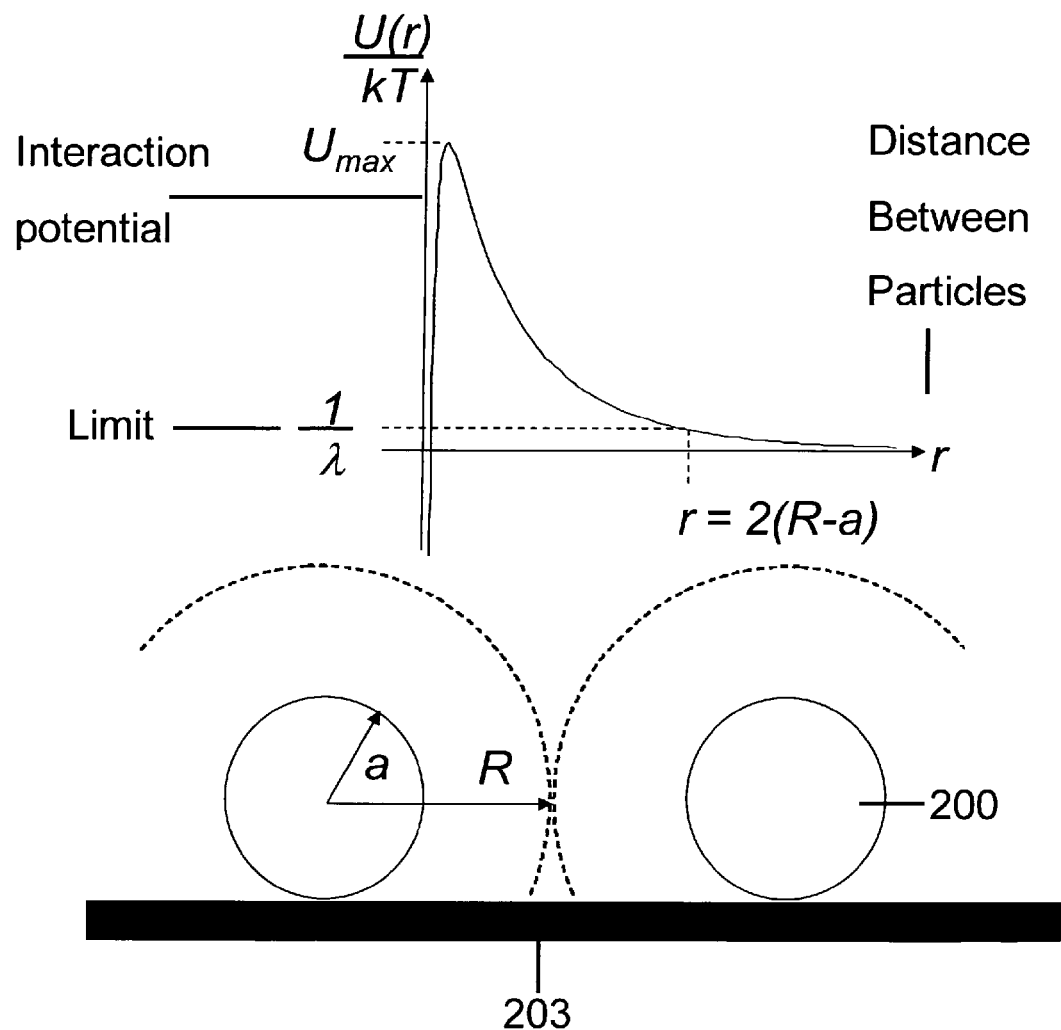
FIG. 3 is an illustration of the physics of the DLVO theory.

The method of diffusion described in relation to FIG. 1 and earlier publications [11] has technical similarities with the described invention, but differs on several crucial aspects. The most important differences are: the component, nanoparticles, which will bind to the surface, is present as a constant concentration and does not diffuse as a gradient; the salt which diffuses does not bind to the surface; the gradient creating factor (gradient electrostatic repulsion between nanoparticles) takes place in the solution on the nanoparticles and not on the surface.

2. Two-dimensional Diffusion

Figure 6A:
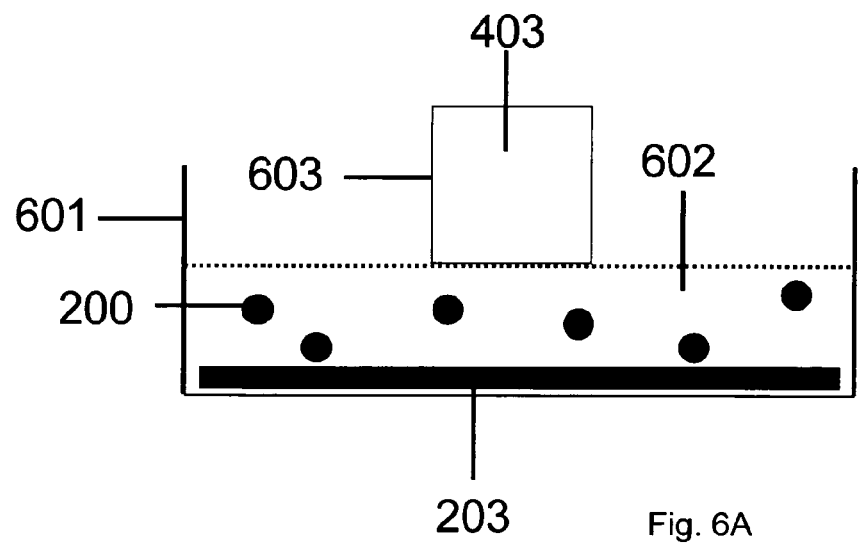
FIG. 6 is an illustration of an embodiment for making circular gradients.
Figure 6B:
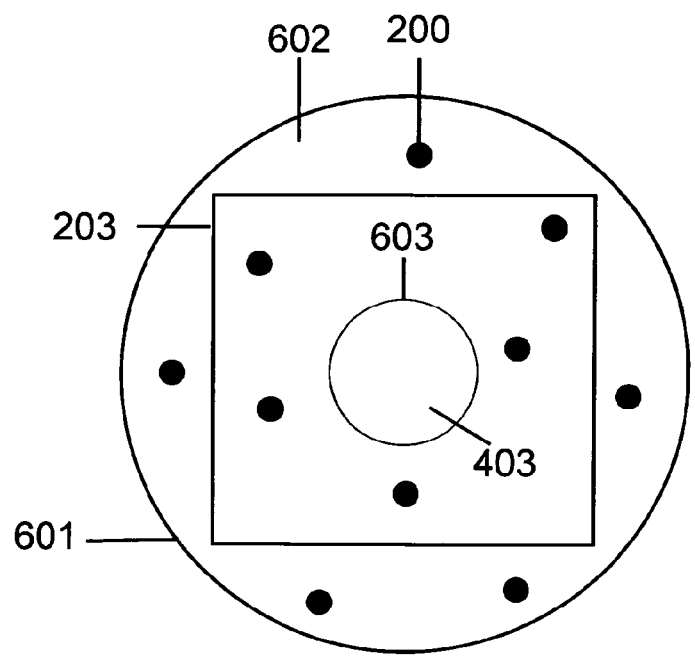
Figure 6C:
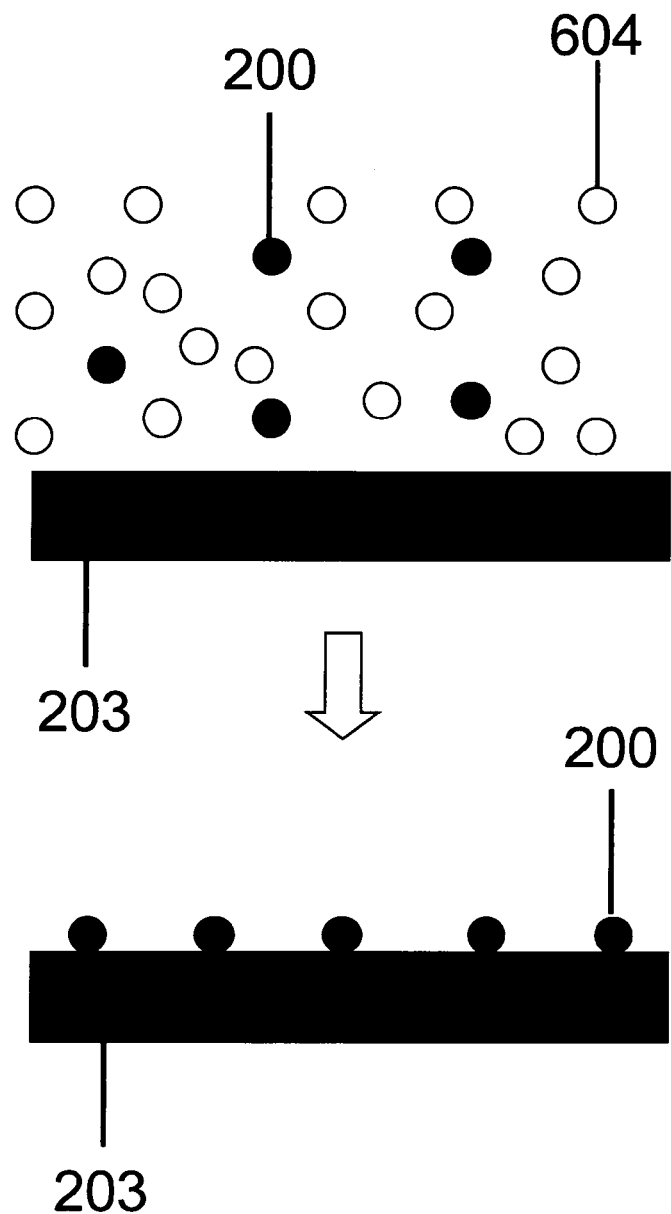

With the one-dimensional method of diffusion gradient surfaces are acquired in one dimension, e.g. high density of bound particles at one en of the gradient and a lower density in the opposite end. In an embodiment according to FIG. 6, making of circular gradients of particles on a surface is described. FIG. 6A is a side view and FIG. 6B is a top view.

On the bottom in a Petri dish 601, a plane surface 203 is placed. A salt free, or almost salt free suspension 602 comprising nanoparticles and a matrix that allows diffusion of nanoparticles but at the same time prevent convection currents, is poured into the Petri dish. Such a suspension can consist of polysaccharides in a water containing particle form, e.g. gel particles used for gel filtration e.g. Sephadex g-25 or similar material. After a free solvent, e.g. water, is removed from the plane suspension layer, a reservoir 603, such as a round piece of blotter, is placed on the suspension. The reservoir 603 is previously filled with the salt solution 403 with high molarity, for example by soaking a blotter in such a solution. This system is then given time for diffusion. The solution 403 will diffuse in the suspension 602 and the circular diffusion front will after a while reaches the surface 203 which eventually will result in a circular surface with a radial concentration gradient of ions. Finally, the suspension 602 is flushed away with a solvent, e.g. water. The end result is a circular surface of adsorbed particles which density is highest in the middle of the surface and lowest towards the periphery.

An important aspect of the described invention is the analytical dynamics, which is the range between that part of the surface gradient with the highest number of adsorbed particles per surface unit and the part of the same gradient surface with the lowest number of adsorbed particles per surface unit. The greater this range is, the more analytical information is obtained in adhesion and adsorption experiments. A methodological source of error can be electrically particles in low concentration in a salt free solvent such as water has a tendency to bind irregularly to surfaces in unpredictable patterns. Such irregular patterns make the interpretation of additional adhesion and adsorption experiments more difficult. In an embodiment according to FIG. 6C a method to prevent the formation of irregular patterns is provided. The method comprises mixing electrically charged, surface binding particles 200 with the electrically charged particles 604 which do not bind to the surface 203. The function of the latter particles is to improve the dispersion of the charged and the binding particles in the solution in order for pattern of binding not to become irregular.

Typical Experiments and Evaluation Methods

A gradient area with bound particles is normally between 1-50 mm, such as 1-10 mm. On this surface adsorption experiments with biopolymers and adhesion experiments with cells can be performed. The result of the experiments can then be correlated to a continuous gradient of bound nanoparticles per surface unit. In simple biopolymer adsorption experiments it is possible to use surface sensitive, optical methods. In experiments involving whole cells light microscopy can be used for detailed studies of the cells as well as fluorescent microscopy for studies of fine details.

Figure 7A:
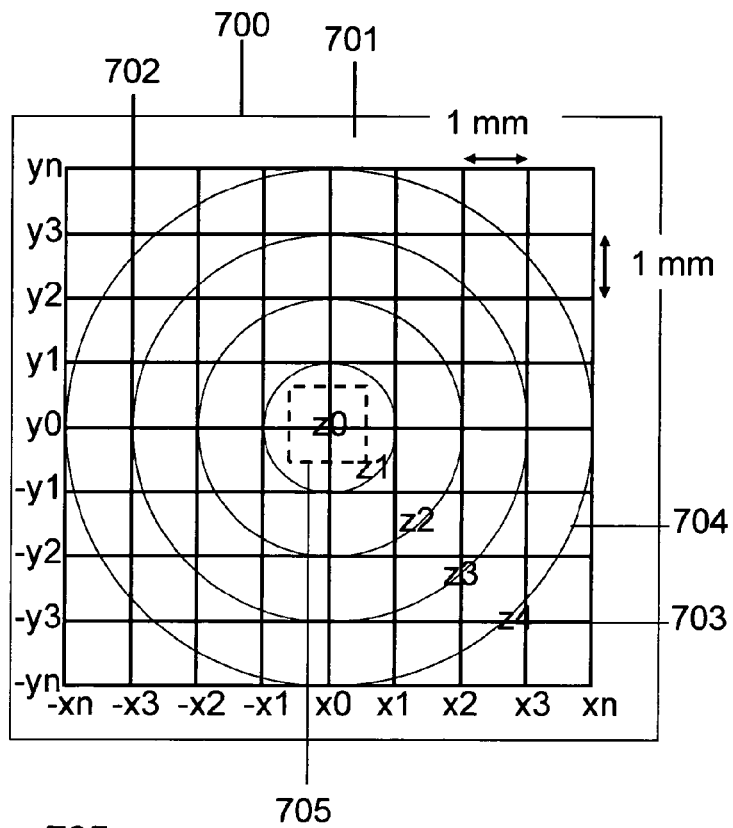
FIG. 7 is an illustration of an embodiment with a circular gradient and scale marks applied to a surface.
Figure 7B:
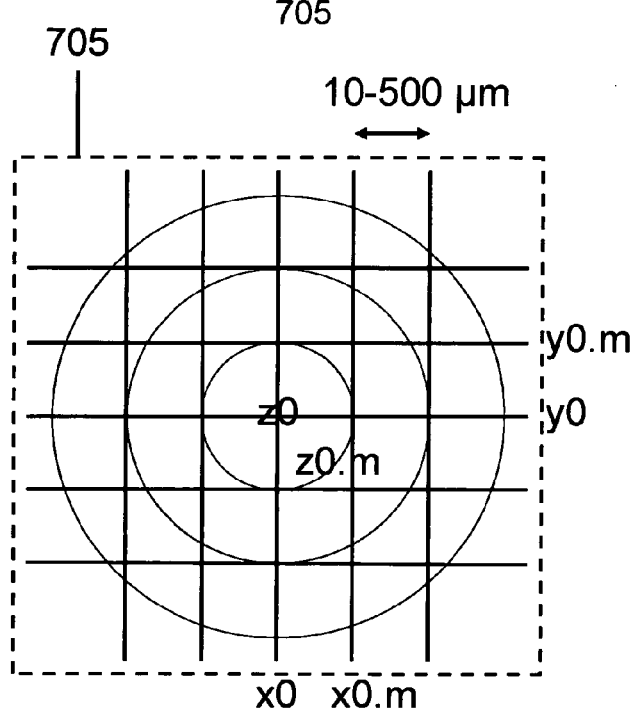

In one application of the invention, FIG. 7, the particle gradient is applied to a surface 700 to which a scale has been added to facilitate the analysis through a microscope. The scale marks can be vertical 702, horizontal 703 or radial 704. The scales and the scale marks can be in different ranges to accommodate different types of analysis e.g. mm range for ocular analysis or 10-500 micrometers range for the analysis for light microscopy or SEM which is described in FIG. 7B, 705. The scale marks can consist of engravings, completely or partly through the particle-binding surface, e.g. a dithiol modified gold surface, so that the underlying substrate, e.g. glass or silica, is exposed. Alternatively, the scale marks can be ridges, e.g. in gold, on a particle-binding surface, e.g. a thiol silane modified glass or silica surface. The surface pattern is preferably made with photo lithographical techniques.

Figure 8A:
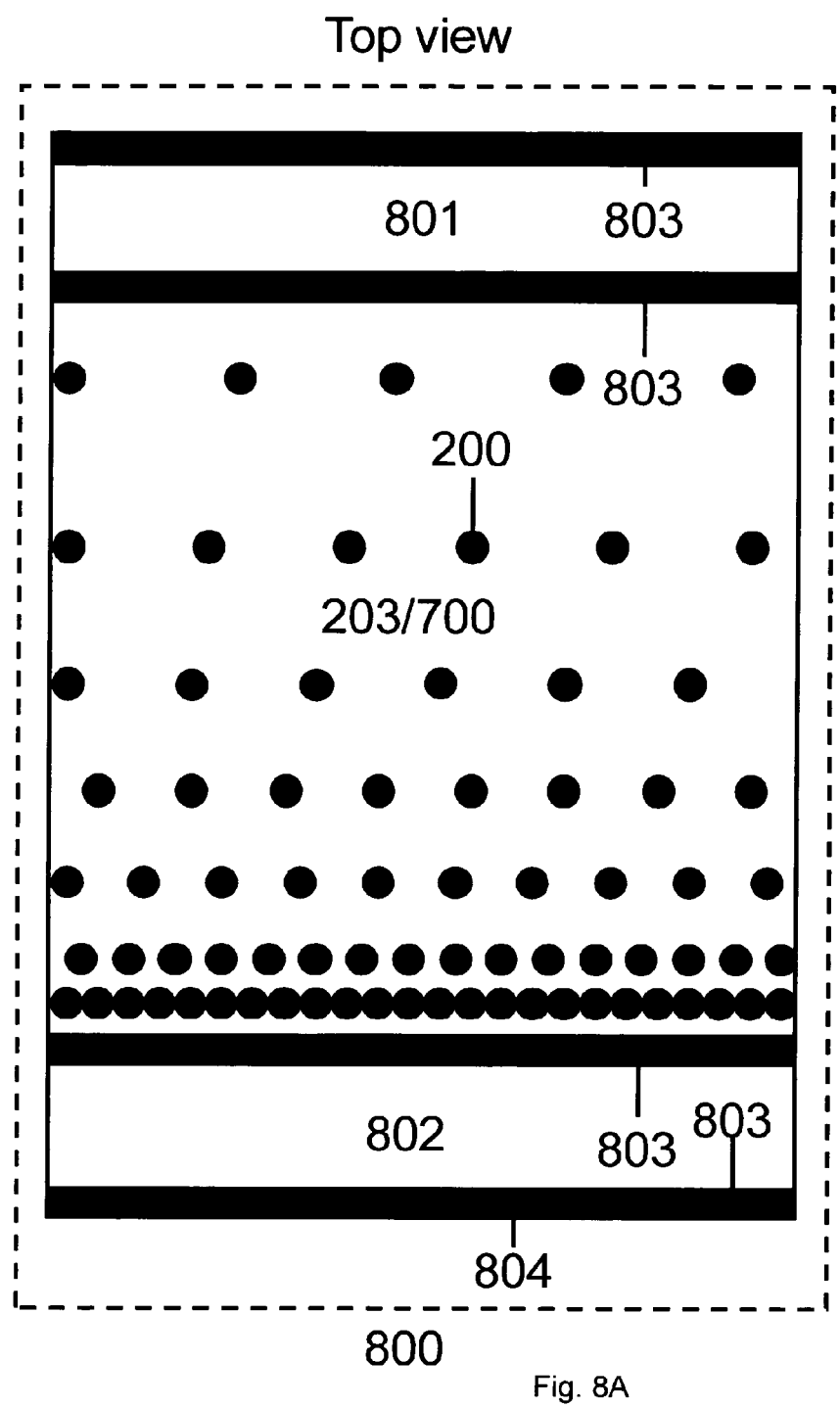
FIG. 8 is an illustration of a surface with a gradient and two separate reference surfaces.
Figure 8B:
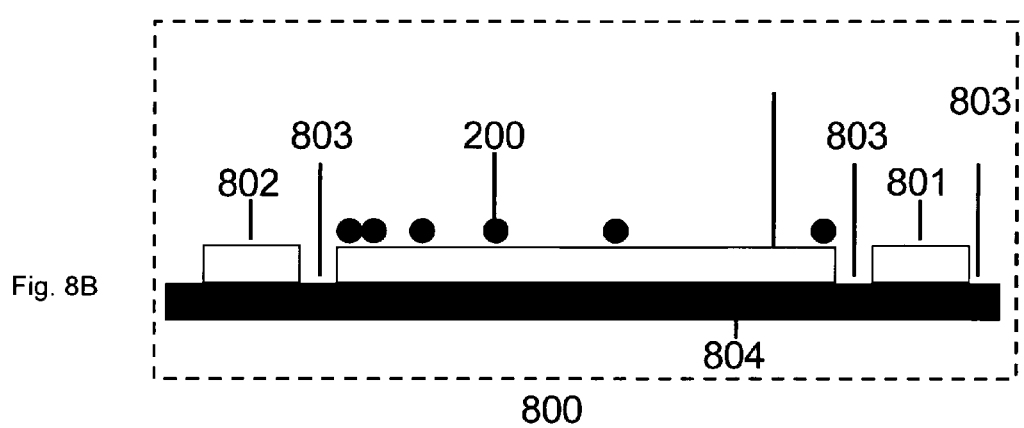
Figure 8C:
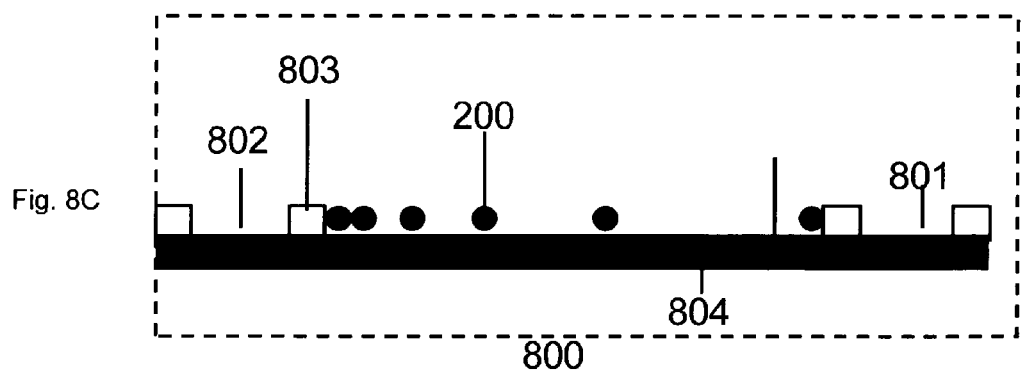

In another application of the invention, FIG. 8, a nanoparticle gradient surface 203 or 700 is present on a chip surface 800, e.g. a glass slide, together with two additional, separate surfaces 801 and 802. FIG. 8A is a top view and FIG. 8B and 8C are side views according to two embodiments. The two additional, separate surfaces are chemically modified in such a way that one of the surfaces 802 is given the same surface chemistry as the surface with the nanoparticles, whereas the other surface 801 is given the same chemistry as the surface that surrounds the particles in the gradient. When all three surfaces are present in a biological experiment, e.g. bacterial adsorption, the operator can examine through a microscope whether the bacteria adsorbs to an area of the gradient surface. The operator also obtains information regarding how the bacteria adsorb to surfaces that do not contain nanoparticles but only unmixed surface chemistries. In this way the operator can determine whether the adhesion of the bacteria is related to the presence of nanoparticles or not, and which particle density is necessary for adsorption. The different surfaces 203/700, 801, an 802 can be separated on the chip 800 with the help of barriers 803 in order to facilitate the use and fabrication of the surface. The barriers can be made of engravings or spaces between the surfaces 203/700, 801, and 802 on the chip 800 in such a way that the underlying substrate 804 is exposed. Alternatively, the barriers can consist of ridges between the surfaces 203/700, 801, and 802, specifically in those cases where the particle gradient has been applied on the underlying substrate 804.

An application of the invention is a product, e.g. a chip comprising a surface, e.g. a glass slide with the three surfaces mentioned above; 1, gold nanoparticle gradient surface where the gold nanoparticle gradient is manufactured on a dithiol modified gold surface on which free dithiols between the particles has reacted with malemide-PEG and the surface of the particles has reacted with a functional thiol, e.g. methyl terminated, amino terminated, acid terminated, or peptide terminated; 2, a gold surface which has been modified dithiol and malemide-PEG; 3, a gold surface which has been modified with the same functional thiol as the surface on the particles.

An application of the invention is a product comprising a surface, e.g. glass slide with the three surfaces mentioned above; 1, gold nanoparticle gradient surface where the gold nanoparticle gradient is manufactured on a dithiol modified gold surface on which free dithiols between the particles has reacted with a malemide-conjugated molecule, e.g. methyl terminated, amino terminated, acid terminated, or peptide terminated, phosphorylated, heterocyclics, aromatics, carbonyles, sugars, inorganics, metal containing particles and the surface of the particles has reacted with a PEG-conjugated thiol 2, a gold surface which has been modified with dithiol and malemide-conjugated molecules, e.g. methyl terminated, amino terminated, acid terminated, or peptide terminated; 3, a gold surface which has been modified with the same functional thiol as the surface on the particles.

An application of the invention is a product comprising a surface, e.g. glass slide with the three surfaces mentioned above; 1, gold nanoparticle gradient surface where the gold nanoparticle gradient is manufactured on a dithiol modified gold surface on which free dithiols between the particles has reacted with malemide-PEG; 2, a gold surface which has been modified dithiol and malemide-PEG; 3, a pure gold surface. With this product, the operator can choose which thiol reagent that should be used. There is a large number of commercially available thiols that can affect adhesion, e.g. thiols conjugated with amino groups, mono- and polysaccharides.

An application of the invention is a product comprising a surface, e.g. glass slide with the three surfaces mentioned above; 1, gold nanoparticle gradient surface where the gold nanoparticle gradient is manufactured on a dithiol modified gold surface; 2, a gold surface which has been modified dithiol; 3 a pure gold surface. With this product the operator can choose both which malemide reagent to be bound between the particles and which thiol reagent to be bound on the particles. The possibilities to alter an experiment will therefore increase further.

An application of the invention is a product comprising a surface, e.g. glass slide with the three surfaces mentioned above; 1, gold nanoparticle gradient surface where the gold nanoparticle gradient is manufactured on a thiol silane modified glass- or silica surface, where free thiol silanes between the particles has reacted with malemide PEG, and where the surface on the particles has reacted with the functional thiol, e.g. methyl terminated, amino terminated, acid terminated, or peptide terminated; 2, a glass or silica surface which has been modified with thiol silane and malemide-PEG; 3, a gold surface which has been modified the same functional thiol as the surface of the particles.

An application of the invention is a product comprising a surface, e.g. glass slide with the three surfaces mentioned above; 1, gold nanoparticle gradient surface where the gold nanoparticle gradient is manufactured on a thiol silane modified glass- or silica surface, where free thiol silanes, between the particles, have reacted with malemide PEG; 2, glass- or silica surface which has been modified with thiol silane and malemide PEG; 3, an unmodified gold surface. With this product the operator can choose which thiol reagent to be used.

An application of the invention is a product comprising a surface, e.g. glass slide with the three surfaces mentioned above; 1, gold nanoparticle gradient surface where the gold nanoparticle gradient is manufactured on a thiol- or aminosilane modified glass- or silica surface, where the silanes under and between the particles has been removed in such a way, e.g. trough plasma treatment, that the particles are sintered on the glass or silica surface where the surfaces between the particles has reacted with PEG-Silane and the surface of the particles has reacted with a functional thiol, e.g. methyl terminated, amino terminated, acid terminated or peptide terminated; 2, a glass or silica surface which has been modified PEG -Silane; 3, a gold surface which has been modified with the same functional thiol as the surface of the particles. An application of the invention is a product comprising a surface, e.g. glass slide with the three surfaces mentioned above; 1, gold nanoparticle gradient surface where the gold nanoparticle gradient is manufactured on a thiol- or aminosilane modified glass- or silica surface and the surface of the particles has reacted with a functional thiol, e.g. PEG terminated, methyl terminated, amino terminated, acid terminated or peptide terminated; 2, a glass or silica surface which has been modified with thiol- or aminosilane; 3, a gold surface which has been modified with the same functional thiol as the surface of the particles.

An application of the invention is a product comprising a surface, e.g. glass slide with the three surfaces mentioned above; 1, gold nanoparticle gradient surface where the gold nanoparticle gradient is manufactured on a thiol- or aminosilane modified glass- or silica surface, where the silanes under and between the particles has been removed in such a way, e.g. trough plasma treatment, that the particles are sintered on the glass or silica surface where the surfaces between the particles have reacted with PEG-Silane; 2, a glass or silica surface which has been modified PEG-Silane; 3, an unmodified gold surface. With this product an operator can choose which thiol reagent to be used.

An application of the invention is a product comprising a surface, e.g. glass slide with the three surfaces mentioned above; 1, gold nanoparticle gradient surface where the gold nanoparticle gradient is manufactured on a thiol- or aminosilane modified glass- or silica surface, where the silanes under and between the particles has been removed in such a way, e.g. trough plasma treatment, that the particles are sintered on the glass or silica surface; 2, a glass or silica surface; 3, an unmodified gold surface. With this product the operator can choose which surface chemistry and method of modification for the different surfaces.

For the above-mentioned applications the three typical surfaces can in manufacturing be made separate, and then be combined on the glass slides with an adhesive. It is also possible to prepare these surfaces directly on a glass slide.

Figure 9:
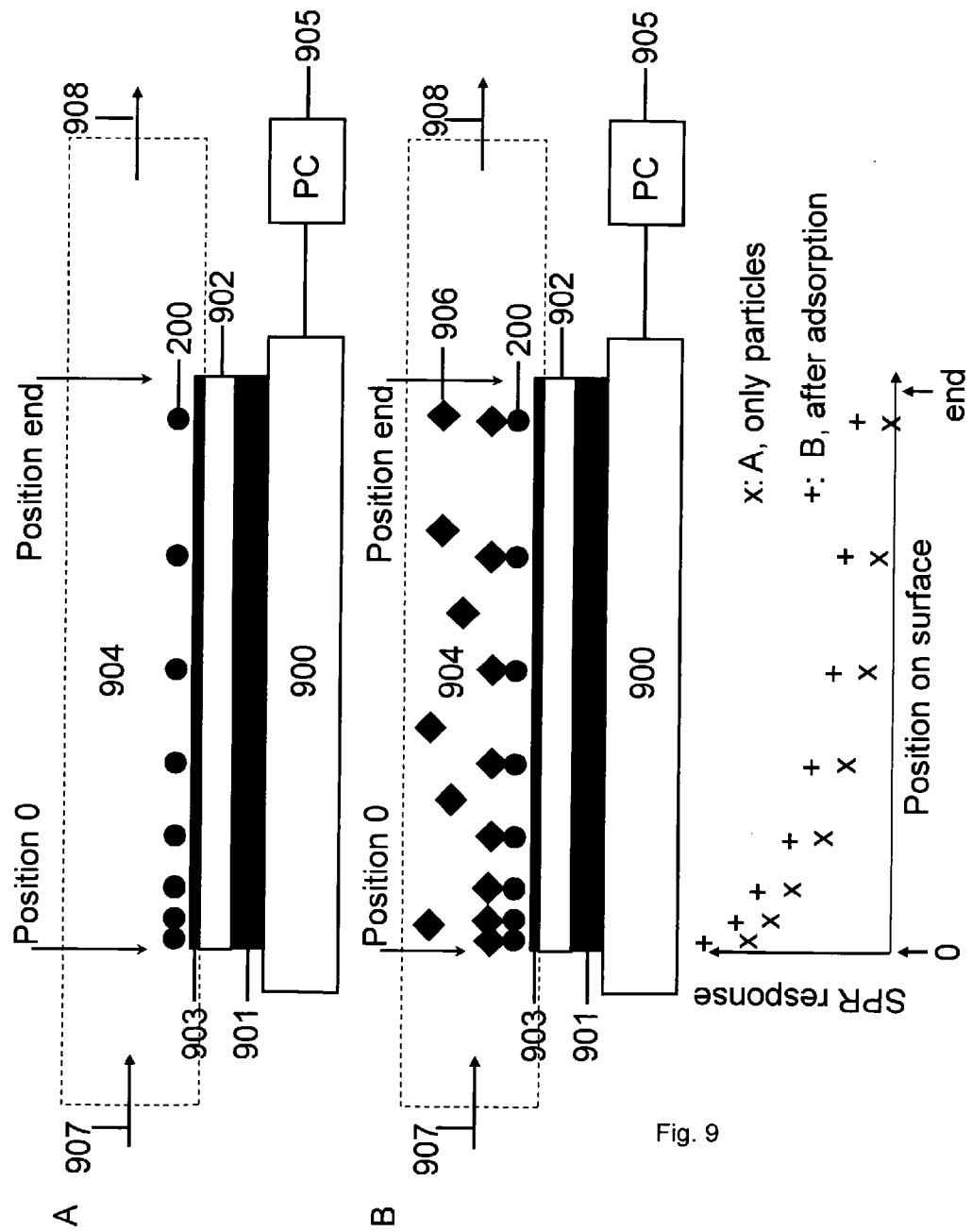
FIG. 9 illustrates a set up for iSPR analysis.

For simple biopolymer adsorption experiments, surface sensitive optical methods such as ellipsometry and surface plasmon resonance (SPR) can be used. A special case of SPR is that so called imaging SPR (iSPR) method which allows for simultaneous quantification of both adsorbing nanoparticles and the following bio adhesion in a complete gradient area (see example). A set up for iSPR analysis of a gradient surface is illustrated in FIG. 9A. An apparatus 900 for imaging SPR such as described in [17], normally controlled with a computer 905, is applied in contact with an SPR-substrate usually comprising a glass surface 901 on which a thin gold layer 902 has been applied. Above the gold layer a chamber 904 containing a solution is placed, e.g. a buffer in such a way that the gold layer is in contact with the solution. The chamber 904 can have an inlet 907 and an outlet 908 and function as a perfusion system to transport solution and analytes to and from the surface.

In an application of the invention the gold surface 902 has been chemically modified with the layer 903 to bind nanoparticles from solution, and a gradient of nanoparticles has been applied to the surface. At analysis the SPR-response from different positions on the gradient surface can be correlated to partial density at this position. In the case bio adhesion, e.g. protein-, thrombocyte-, or bacterial adsorption takes place to the gradient surface this can also be detected as an additive response, FIG. 9B.

Figure 10:
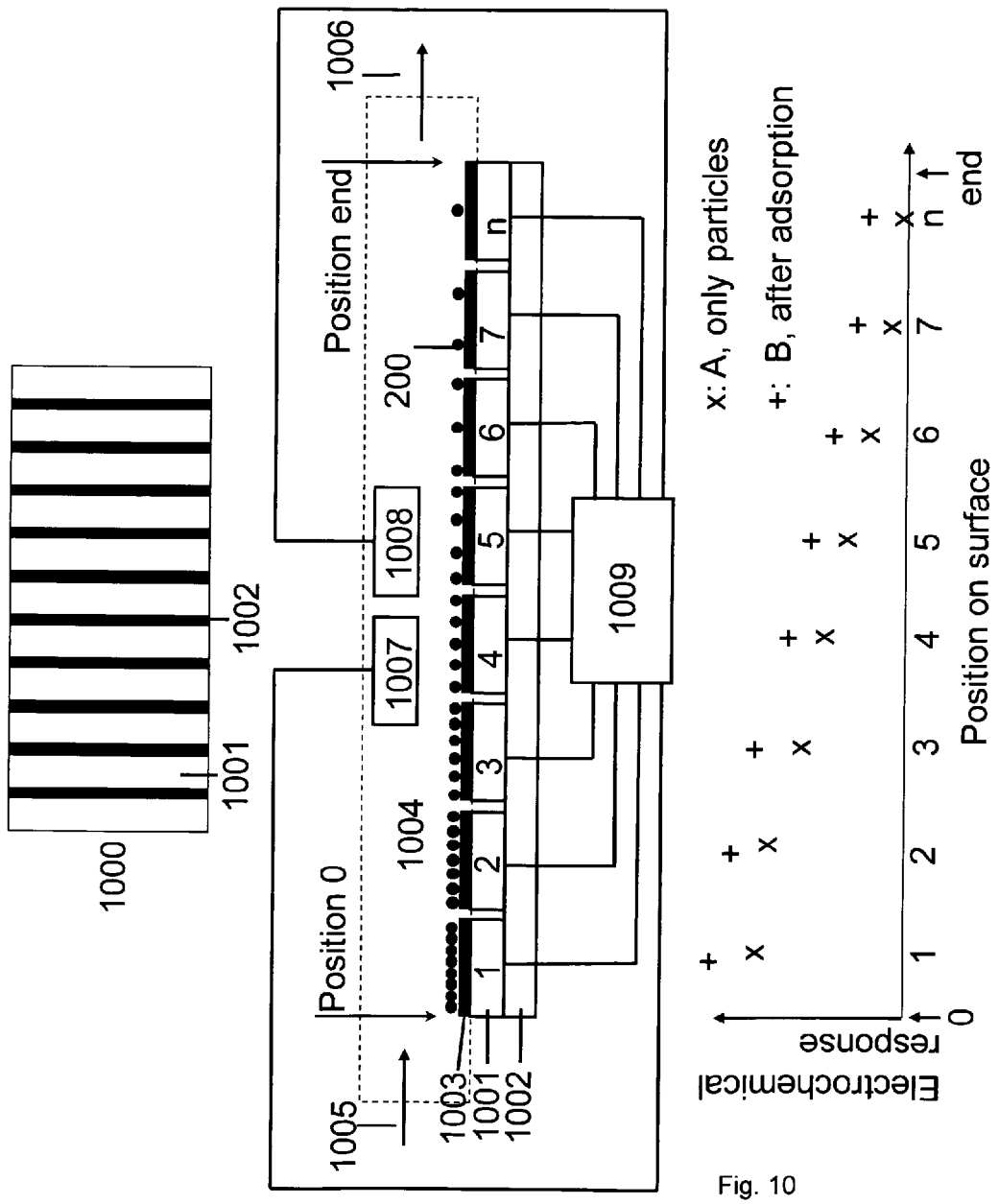
FIG. 10 illustrates an application of the present invention for studying cell interactions with surfaces.

Lately, electrochemical technologies, particularly measurements of impedance have been used to study cell interactions with surfaces [18]. Electrochemical technologies can also be used to estimate the number of nanoparticles on an electrode surface. This specifically is true for conducting nanoparticles for instance gold [19]. In an application of the invention described in FIG. 10 a nanoparticle gradient is applied on a surface 1000 which is made up of n particle binding surfaces 1001 of an electrically conducting material which has been modified with the chemistry 1003 to bind nanoparticles. The surfaces 1001 is place on a non conducting substrate 1002 in such a way that the surfaces 1001 an act as electrodes electrically isolated from one and other. The nanoparticle gradient is manufactured in such a way that the particle binding electrode surface 1 on the surface 1000 gets a high particle density while the particle binding electrode surface n on the surface 1000 gets low particle density. This is possible by using the surface 1000 such as surface 203 in FIG. 4 and let position 0 on the surface 1000 coincide x=0 in FIG. 4.

The surface 1000 is applied in contact with an electrolyte, e.g. a buffer, in an electrochemical cell 1004 which also can have an inlet 1005 and an outlet 1006 in order to facilitate transportation of electrolyte and analyte to the surface 1000. In addition to the electrodes 1-$n$ localized on the surface 1000, it is necessary for some applications to add an additional reference electrode 1007 and a counter electrode 1008 applied in the electrolyte. In some applications the electrodes 1007 and or 1008 can also be placed on the surface 1000. All electrodes 1-$n$ on the surface 1000 and in some cases 1007 and 1008, are connected individually by a system for electrochemical reference 1009. The system 1009 can be a system capable of different types of electrochemical reference, e.g. voltammetry, amperometry, coulometry, impedance spectroscopy or impedance determination. Alternatively the system 1009 could be a system designed for a single type of electrochemical measurements such as impedance measurements. The electrochemical response from the different electrodes on the surface 1000 can be measured either between different electrodes on the surface 1000, or by using the electrodes 1007 and 1008 in a conventional tri electrode setup [20]. When measuring, the electrochemical response from different electrodes with different positions on the surface 1000 can be correlated to the particle density at this position. If bio adhesion, e.g. cell adhesion, takes place to the gradient surface this can also be detected as an additive, usually a negative, change of the electrochemical response. If a redox active substance comes in contact with the surface this can also be detected as an additive, usually a positive change of the electrochemical response.

EXAMPLE 1

Evaluation of Gradual Particle Adsorption with SEM

Figure 11:
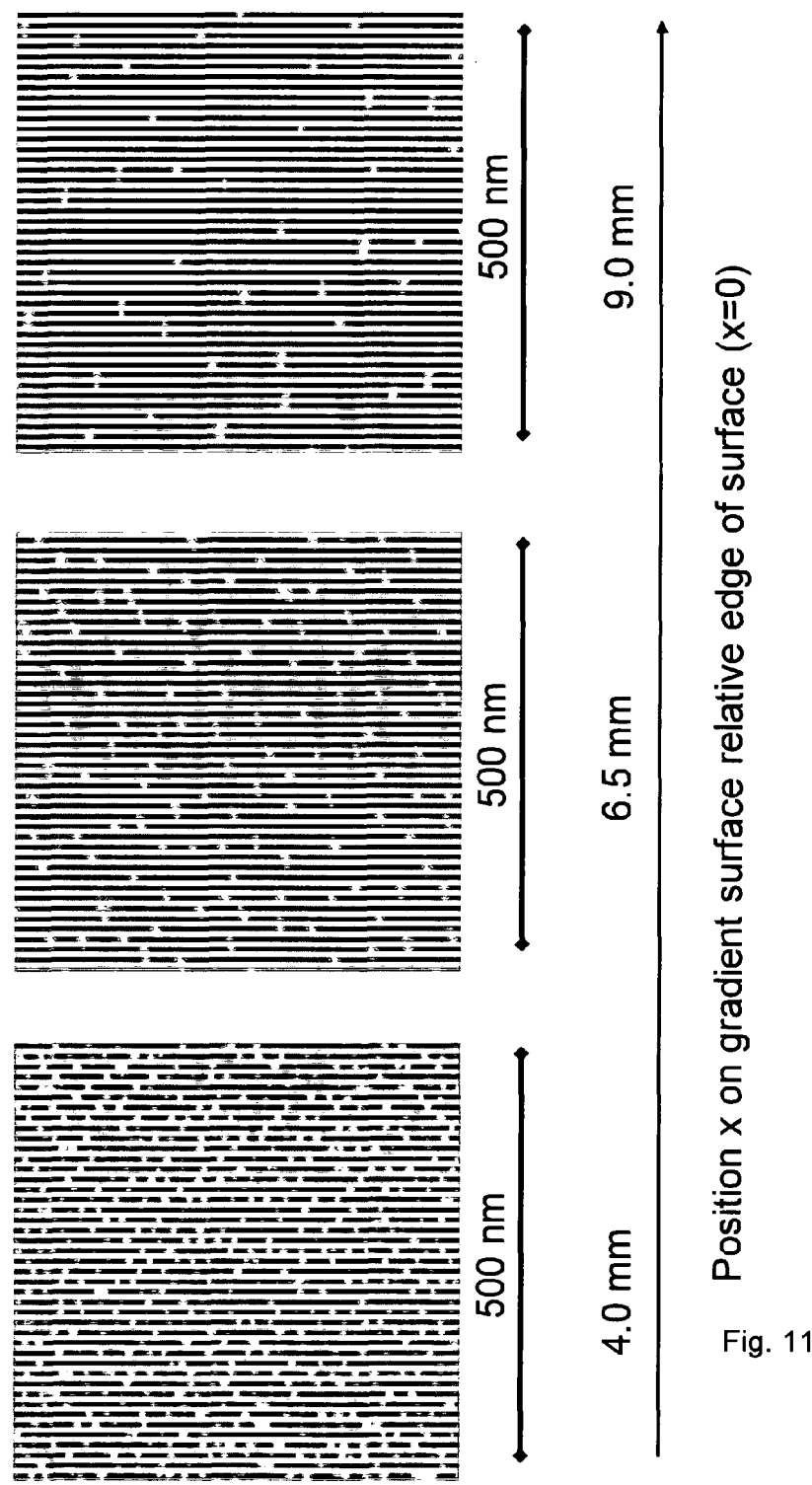
FIG. 11 is an overview of surfaces according to embodiments of the invention, analyzed with SEM.

Gold surfaces with size 11×20 mm were manufactured by evaporation of first 5 nm Cr and then 200 nm Au on a substrate of SiO2. These were washed and provided with a monolayer of dithiol according to the procedure described in detail [1, 8]. In short, the clean gold surfaces were incubated in a solution of octane dithiol in ethanol where they were reactivated with dithiolthreitol (DDT). An electrostatically stabilized gold particle solution with gold particles around 10 nm in diameter was manufactured according to the procedure described in detail [1, 8]. The gold solution was centrifuged at 16000 g to reduce the ionic strength in the solution, and in order to increase the concentration of the particles. After centrifugation the gold particle pellet was diluted to an approximate particle concentration of 55 nM in pure water with the conductivity of 18.2 MΩ*cm. This particle solution was transferred to a container designed gradient manufacturing according to FIG. 5 after which a number of the dithiol prepared surfaces were placed in the same container with a specific distance to the bottom the same. There after a citrate buffer with the concentration 1M and pH 4,0 was placed at the bottom of the gradient container so that the space underneath the surfaces was filled with this buffer. The citrate buffer was then allowed to diffuse over the surfaces during 30 minutes after which the procedure was stopped by emptying the solution from the gradient container from below. In a different application the citrate buffer with the concentration 50 mM was applied underneath the surfaces and was the allowed to diffuse less than 90 minutes which results in a longer gradient with less slope compared to the one obtained with 1 M buffer under 30 minutes. The surfaces were analyzed with SEM at different positions on the gradient surface. A selection of pictures is presented in FIG. 11.

EXAMPLE 2

Evaluation of Gradual Particle Adsorption by iSPR

Figure 12:
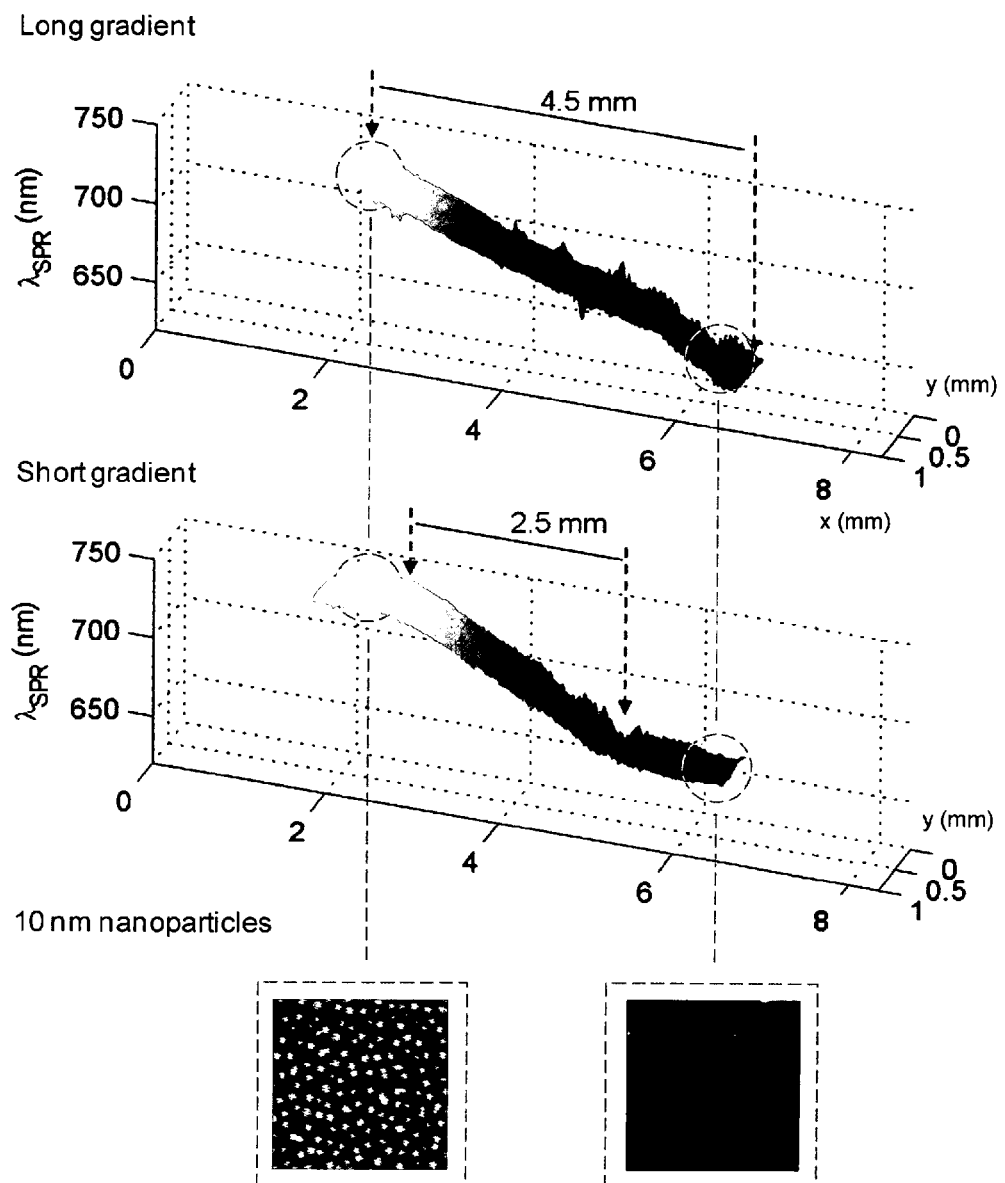
FIG. 12 shows results of two gradients, analyzed with SPR.
Figure 13:
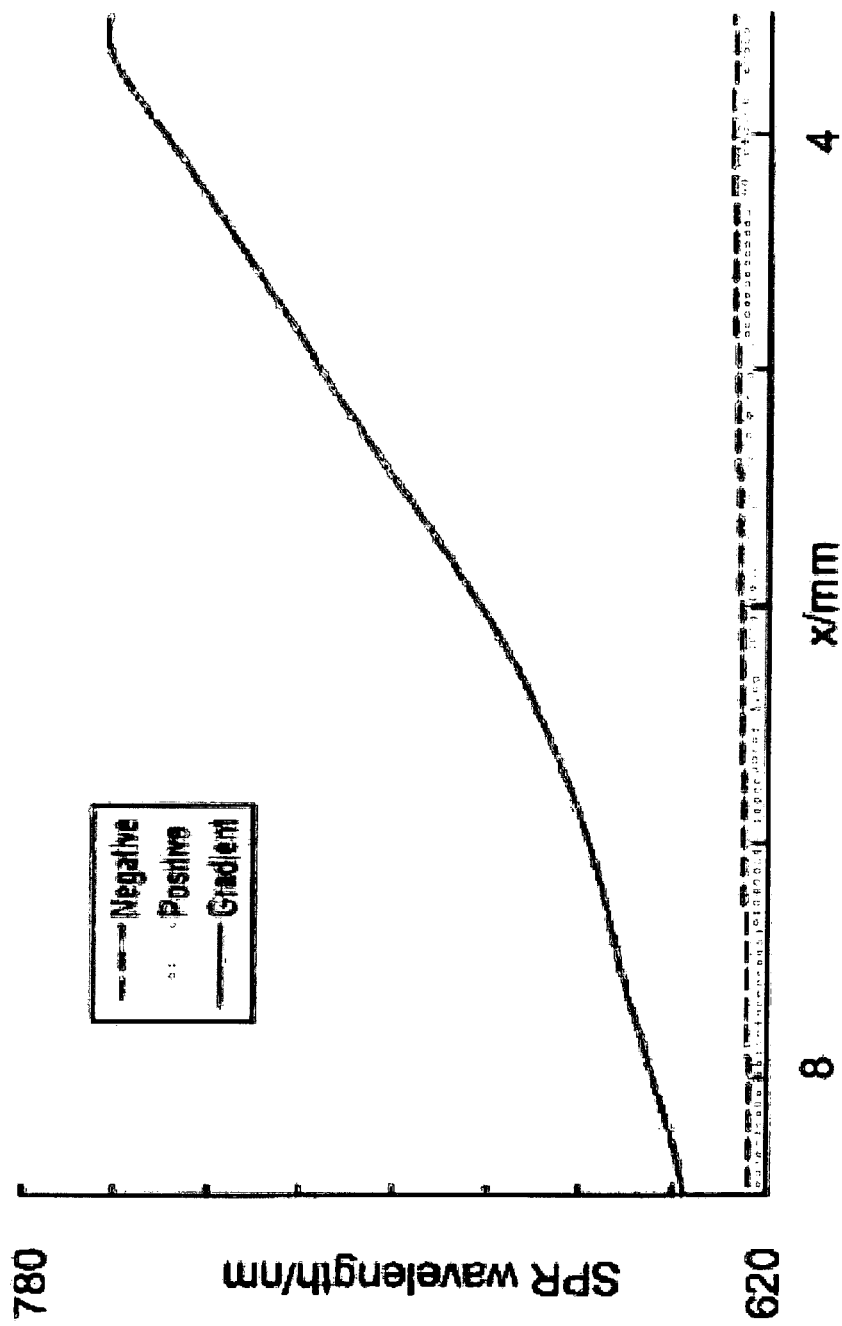
FIG. 13 is a line scan of a gradient according to an embodiment, together with a line scan for a positive control surface.

Linear gradients with 10 nm gold nanoparticles were prepared as described in example 1 by dithiol chemistry. As a substrate glass surfaces on which a thin layer of Au, app. 50 nm, had been evaporated was used. These surfaces are suitable for analysis by surface Plasmon resonance, SPR, after the manufacture of gradients the surfaces were placed in an instrument for imaging SPR which is described in detail in [17]. Two different gradients were analyzed, see FIG. 12. One gradient had been prepared with 50 mM citrate buffer which has been allowed to diffuse for 90 minutes ("long" gradient), and one gradient had been prepared with 1 M citrate buffer for 30 minutes ("short" gradient). Each particle gradient also had reacted with maleimide-PEG in order minimize bioadhesion between the distributed particles, and with octane thiol above the particles which makes the surfaces on the particles hydrophobic in order to promote bio adhesion. On each gradient surface an area of app. 1×5 mm was analyzed. In these areas all essential parts of the gradient was pictured. The SPR wave length presented in the 3D graph z-axis is proportional to the surface coverage of gold nanoparticles. In FIG. 13 a line scan of a "short" gradient is presented together with a line scan for a positive control surface, (in this case a surface modified with only octanedithiol), and a negative control surface modified with octane dithiol and maleimide-PEG. Each line scan represents an average of all scans of the surface.

EXAMPLE 3

Figure 14:
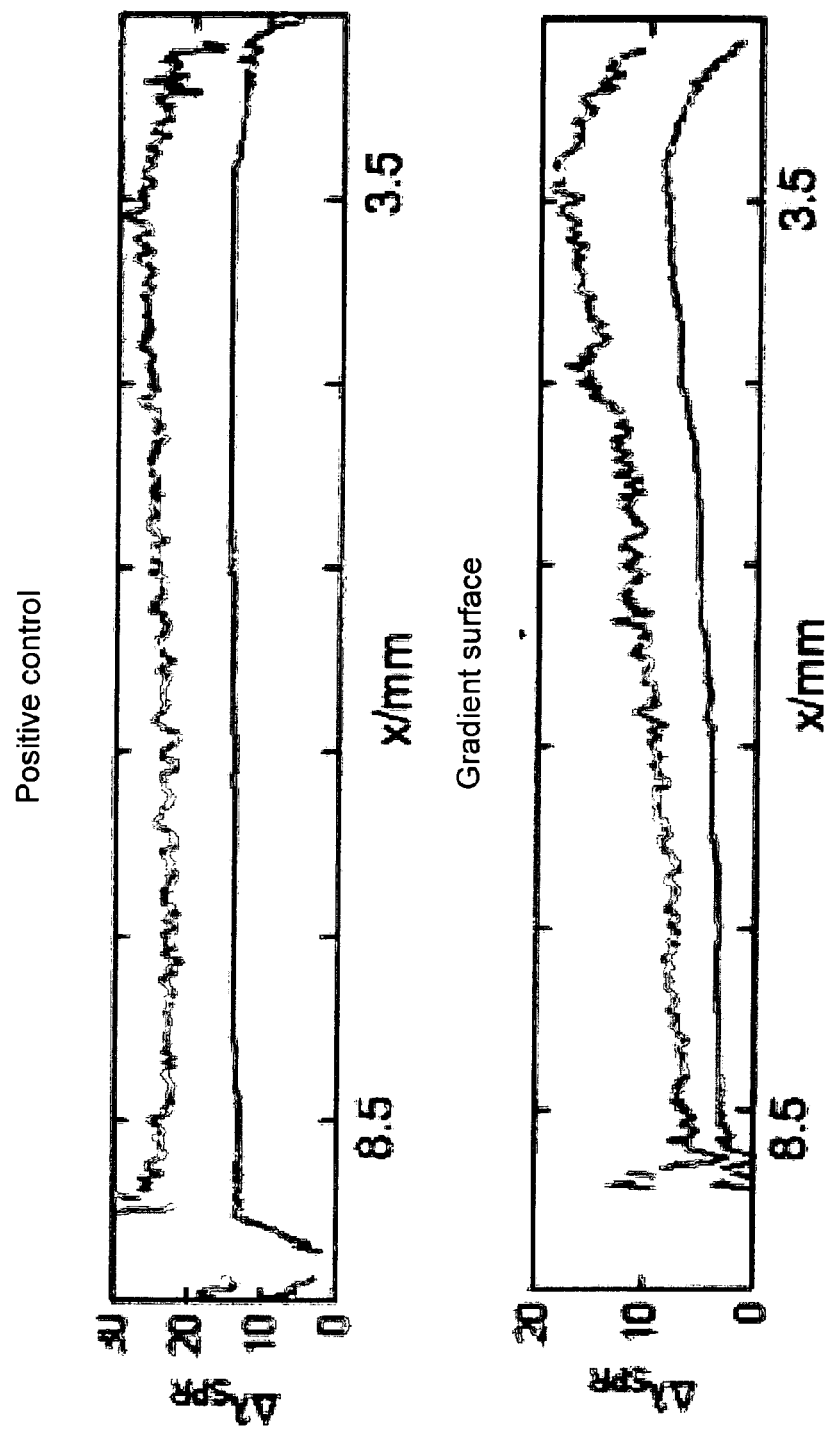
FIGS. 14 to 16 are results of analyses according to embodiments of the invention.
Figure 15:
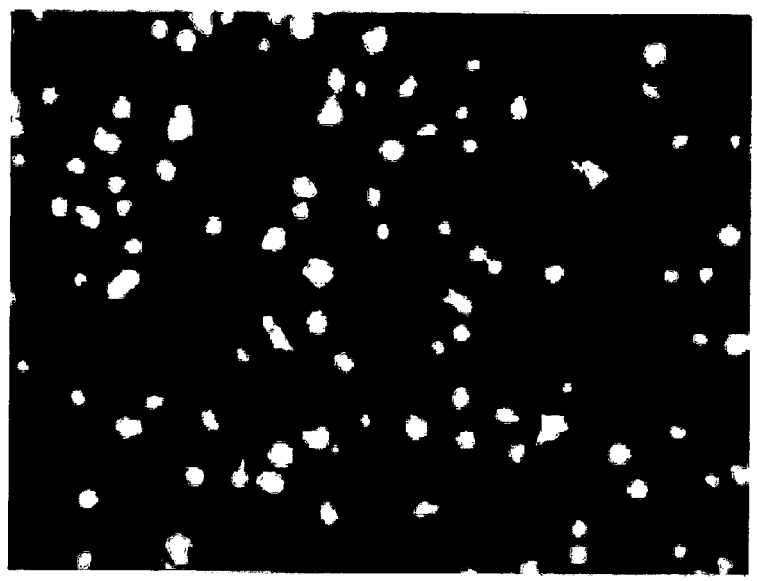
Figure 15:
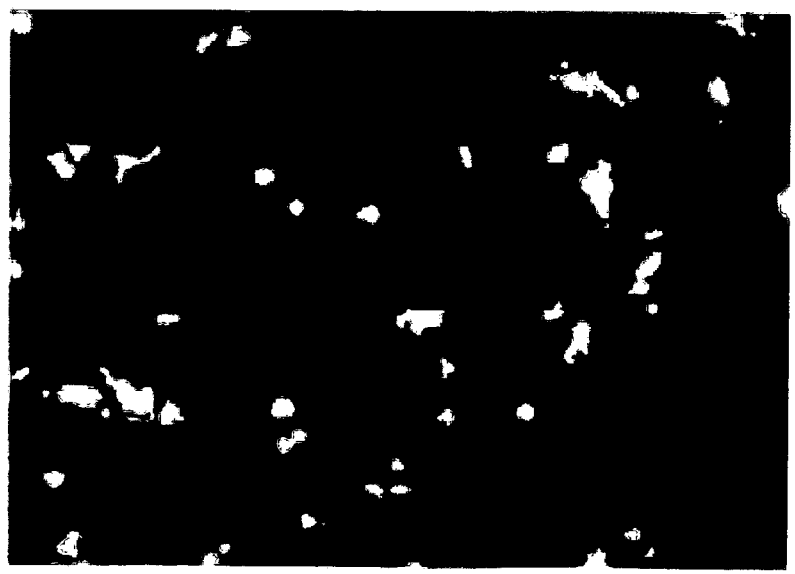

Evaluation of Fibrinogen Adsorption and Thrombocyte Adsorption to Hydrophobic Nanoparticle Gradients with iSPR and Fluorescence Microscopy "Short" gradients with 10 nm gold nanoparticles were manufactured on gold surfaces designed for SPR analysis, and were then modified by malemide-PEG and octanethiol according to example 2 above. This gives gradients of hydrophobic particles against the background of protein rejecting PEG. The surfaces were analyzed with iSPR. In a sequence fibrinogen (0.5 mg/ml in PBS) for 5 minutes and then thrombocytes (essentially a serum free preparation from a healthy donor) for 30 minutes were adsorbed to surfaces with gradients, positive control surfaces (only dithiol), and negative control surfaces (dithiol modified with malemide-PEG). In FIG. 14 the response from fibrinogen and thrombocyte adsorption is presented for a gradient surface and a positive controlled surface. The blue curve shows the adsorption of fibrinogen, the green curve the accumulated response from both fibrinogen and thrombocytes. The response from the underlying surfaces, corresponding to what is shown in FIG. 13, has been subtracted from the results in FIG. 14. Note that the positive surface adsorbs both fibrinogen and thrombocytes homogeneously across the surface, while the gradient surface adsorbs both protein and thrombocytes gradually. The negative control surfaces gave no significant response. After thrombocyte adsorption the surfaces were washed with PBS buffer and fixated for 15 minutes with 2% glutaraldehyde. The surfaces were stained (staining of the actin skeleton) according to a normal protocol and were analyzed fluorescence microscopy at different positions at the surfaces. FIG. 15 shows representative thrombocytes at positions with high (A) and low (B) particle coverage respectively.

EXAMPLE 4

Evaluation of Microbial Adhesion to Hydrophobic Nanoparticle Gradients.

Figure 16:
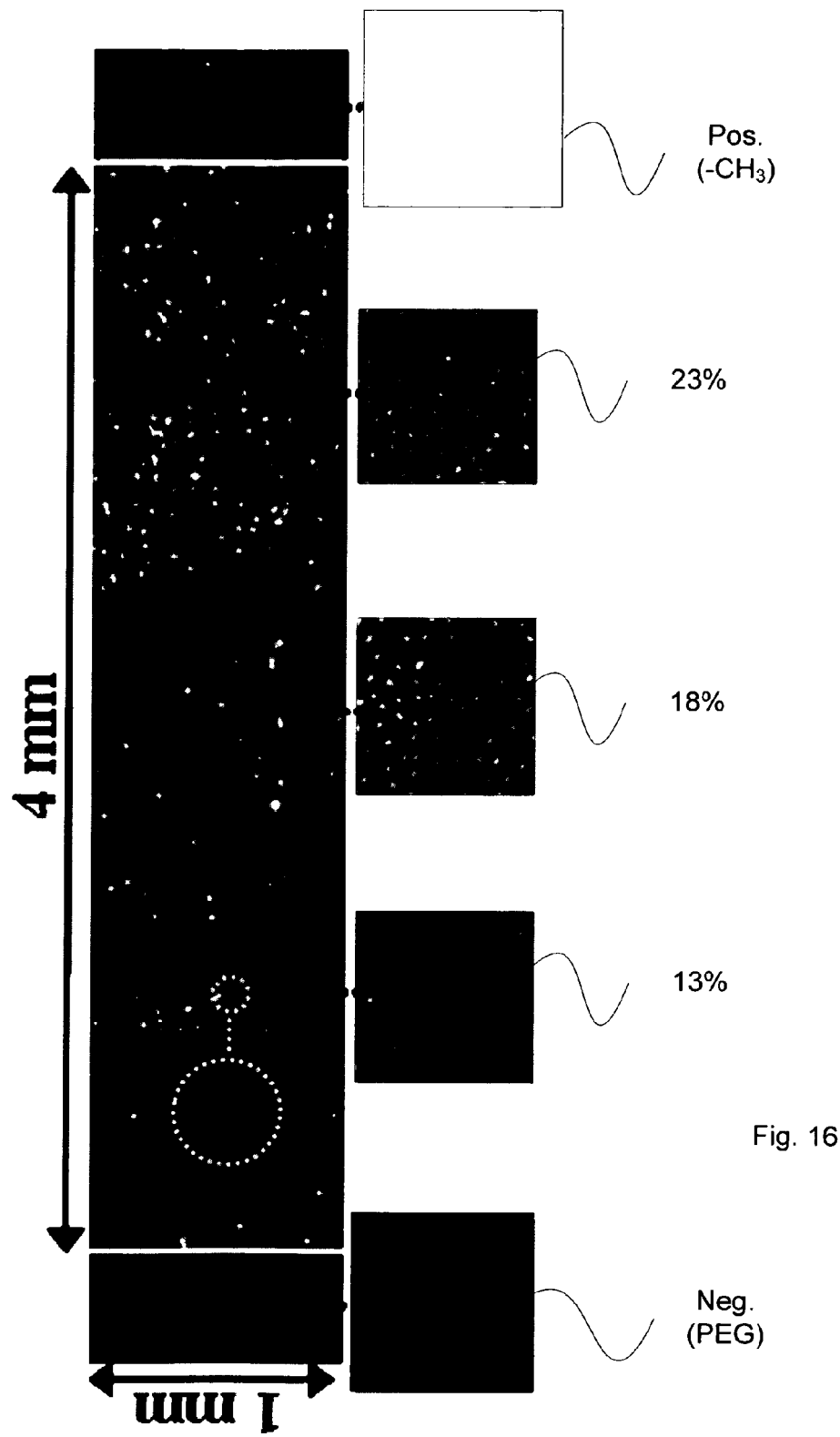

"Long" gradients with 10 nm gold nanoparticles were manufactured on gold surfaces modified with malemide-PEG and octane thiol according to example 2 above. This gives gradients with hydrophobic particles against the background of protein rejecting PEG. Fimbriated *E. coli* were adsorbed to the surfaces under static conditions, and were exposed to a controlled wash for 10 minutes. Remaining bacteria were stained with acridine orange and DAPI after which the surfaces were analyzed under magnifying glass and fluorescence microscopy. FIG. 16 shows a section of a gradients surface with adsorbed *E. coli* stained with acridine orange at low magnification together with a positive control surface (octane thiol) and negative control surface (dithiol modified with malemide-PEG). The surface coverage of nanoparticles at different positions in the gradient was determined by SEM. The relative surface coverage is shown in each picture. The inserted picture shows two bacteria stained with DAP at greater magnification. The distribution of bacteria changes dramatically at 20% surface coverage.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

REFERENCES

1. Lundgren A. O., et al., *Self-Arrangement Among Charge-Stabilized Gold Nanoparticles on a Dithiothreitol Reactivated Octanedithiol Monolayer.* Nano Letters, 2008. 8(11): p. 3989-3992.

2. Adamczyk Z., et al., *Structure and ordering in localized adsorption of particles.* Journal of Colloid and Interface Science, 1990. 140(1).

3. Hanarp P., et al., *Control of nanoparticle film structure for colloidal lithography.* Colloids and Surfaces A: Physicochemical and Engineering aspects, 2003. 214: p. 23-36.

4. Johnson C. A. and Lenhoff A. M., *Adsorption of charged latex particles on Mica studied by atomic force microscopy.* Journal of Colloid and Interface Science, 1996. 179: p. 587-599.

5. Semmler M., et al., *Diffusional deposition of charged latex particles on water-solid interfaces at low ionic strength.* Langmuir, 1998. 14: p. 5127-5132.

6. Kooij E. Stefan, et al., *Ionic strength mediated self-organisation of gold nanocrystals: an AFM study.* Langmuir, 2002. 18: p. 7677-7682.

7. Verwey E. J. W. and Overbeek J. Th. G., *Theory of the stability of lyophobic colloids.* 1948, Amsterdam: Elsevier Publishing Company Inc.

8. Lundgren A. O., PCT/SE2009/051060. 2009.

9. Arnold M., et al., *Activation of integrin function by nanopatterned adhesive interfaces.* ChemPhysChem, 2004. 5: p. 383-388.

10. Michel R., et al., *A novel approach to produce biologically relevant chemical patterns at the nanometer scale: selective molecular assembly patterning combined with colloidal lithography.* Langmuir, 2002. 18: p. 8580-8586.

11. Elwing H., et al., *A wettability gradient-method for studies of macromolecular interactions at the liquid solid interface.* Journal of Colloid and Interface Science, 1987. 119(1): p. 203-210.

12. Kim M. S., Khang G., and Lee H. B., *Gradient polymer surfaces for biomedical applications.* Progress in polymer science, 2008. 33(1): p. 138-164.

13. Morgenthaler S., Zink C., and Spencer N.D., *Surface-chemical and—morphological gradients.* SOFT MATTER, 2008. 4(3): p. 419-434.

14. Liedberg B. and Tengvall P., *Molecular gradients of omega-substituted alkanethiols on gold—preparation and characterization.* Langmuir, 1995. 11(10): p. 3821-3827.

15. Grabar Katherine C., et al., *Kinetic control of interparticle spacing in Au colloid-based surfaces: Rational nanometer-Scale Architecture.* Journal of the American Chemical Society, 1996. 118: p. 1148-1153.

16. Arnold M., et al., *Induction of cell polarization and migration by a gradient of nanoscale variations in adhesive ligand spacing.* Nano Letters, 2008. 8(7): p. 2063-2069.

17. Andersson O., et al., *Gradient Hydrogel Matrix for Microarray and Biosensor Applications: An Imaging SPR Study.* Biomacromolecules, 2009. 10: p. 142-148.

18. K→owino I. O. and Sadik O. A., *Impedance spectroscopy: A powerful tool for rapid biomolecular screening and cell culture monitoring.* Electroanalysis, 2005. 17(23): p. 2101-2113.

19. Zhao J. J., et al., *Nanoparticle-mediated electron transfer across ultrathin self-assembled films.* Journal of Physical Chemistry B, 2005. 109(48): p. 22985-22994.

20. Bard A. J. and Faulkner L. R., *Electrochemical Methods.* 2:nd ed. 2001: John Wiley & Sons Inc.

The invention claimed is:

1. A method for preparing a continuous gradient of deposited and electrically charged nanoparticles along a solid surface, comprising:
   immersing the solid surface into a solution comprising electrically charged nanoparticles;
   diffusing a salt solution into the solution comprising the electrically charged nanoparticles and the solid surface, the salt solution diffusing along the solid surface and creating a salt concentration gradient in the solution comprising the electrically charged nanoparticles; and
   depositing the electrically charged nanoparticles on the solid surface;
   wherein the density of electrically charged nanoparticles that are deposited on the solid surface forms a gradient as a result of the salt concentration gradient; and
   wherein the distance between the electrically charged nanoparticles is regulated through controlling electrostatic repulsion amongst the electrically charged nanoparticles.

2. The method of claim 1, wherein the diffusion of salt solution is obtained by forming a layer of a salt solution under a layer of substantially salt free solution comprising the nanoparticles, and wherein the continuous gradient of electrically charged nanoparticles is regulated by the time of diffusion and concentration of the salt in the salt solution.

3. The method according to claim 1, wherein the diffusion of the salt solution is obtained by keeping the salt solution in a reservoir, placed into contact with the solution comprising the nanoparticles, the nanoparticles being suspended in the solution, said solution further comprising a matrix allowing diffusion of the nanoparticles but prohibiting convection currents, and which solution comprising the nanoparticles is in contact with the solid surface.

4. The method according to claim 1, wherein the nanoparticles consist of a material selected from the group consisting of metal, ceramics, glass, and polymer material; and wherein the solid surface consists of a material selected from the group consisting of metal, ceramics, glass, and polymer material.

5. The method according to claim 1, wherein the surface is gold, with bound dithiol reagent and the nanoparticles are covalently bound to thiol groups of the dithiol molecule bound to the gold surface.

6. The method according to claim 1, wherein negatively charged but non-surface binding particles are mixed with surface binding nanoparticles.

7. The method according to claim 1, wherein the solid surface comprises first and second separate surfaces, and wherein the first separate surface has a surface chemistry similar to the nanoparticle and the second separate surface has a surface chemistry similar to the solid surface.

8. The method according to claim 1, further comprising adding scale marks to the surface.

9. The method according to claim 1, further comprising providing a matrix in the solution comprising electrically charged nanoparticles, wherein the matrix allows for diffusion of the nanoparticles and salt solution, but prohibits convection currents.

* * * * *

UNITED STATES PATENT AND TRADEMARK OFFICE
CERTIFICATE OF CORRECTION

| | | |
|---|---|---|
| PATENT NO. | : 9,566,604 B2 | Page 1 of 2 |
| APPLICATION NO. | : 13/818541 | |
| DATED | : February 14, 2017 | |
| INVENTOR(S) | : Anders Lundgren et al. | |

It is certified that error appears in the above-identified patent and that said Letters Patent is hereby corrected as shown below:

In the Specification

Column 3,
Line 3, "has a very" should read --have a very--.
Line 47, "bio adhesion." should read --bioadhesion.--.

Column 4,
Line 39, "has been" should read --have been--.

Column 5,
Line 36, "may comprises" should read --may comprise--.

Column 8,
Line 29, "one en of" should read --one end of--.
Line 47, "reaches" should read --reach--.
Lines 61-62, "electrically particles" should read --electrically charged particles--.
Line 63, "water has" should read --water which has--.

Column 11,
Line 58, "bio adhesion" should read --bioadhesion--.

Column 12,
Lines 8-9, "case bio adhesion," should read --case that bioadhesion,--.
Lines 23-24, "one and other." should read --one another.--.
Line 54, "bio adhesion," should read --bioadhesion,--.

Signed and Sealed this
Fifth Day of September, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,566,604 B2

Column 13,
Line 20, "pH 4,0" should read --pH 4.0--.
Line 57, "bio adhesion." should read --bioadhesion.--.
Line 59, "was pictured." should read --were pictured.--.

Column 14,
Line 35, "analyzed fluorescence" should read --analyzed by fluorescence--.

Column 16,
Line 9, "K→owino" should read --K'owino--.
Line 17, "2:nd ed." should read --2nd ed.--.